(12) United States Patent
Cummins

(10) Patent No.: US 10,758,365 B2
(45) Date of Patent: Sep. 1, 2020

(54) EXPANDABLE SPINAL CAGE ASSEMBLIES FOR SUPPORTING BONE STRUCTURES

(71) Applicant: ZAVATION MEDICAL PRODUCTS LLC, Flowood, MS (US)

(72) Inventor: John Franklin Cummins, Kosciusko, MS (US)

(73) Assignee: Zavation Medical Products, LLC, Flowood, MS (US)

( * ) Notice: Subject to any disclaimer, the term of this patent is extended or adjusted under 35 U.S.C. 154(b) by 43 days.

(21) Appl. No.: 15/974,225

(22) Filed: May 8, 2018

(65) Prior Publication Data

US 2018/0318107 A1 Nov. 8, 2018

Related U.S. Application Data

(60) Provisional application No. 62/502,844, filed on May 8, 2017, provisional application No. 62/633,769, filed on Feb. 22, 2018.

(51) Int. Cl.
 *A61F 2/44* (2006.01)
 *A61F 2/30* (2006.01)
 *A61F 2/46* (2006.01)

(52) U.S. Cl.
 CPC ........ *A61F 2/4465* (2013.01); *A61F 2/30771* (2013.01); *A61F 2/44* (2013.01); *A61F 2/4611* (2013.01); *A61F 2002/3049* (2013.01); *A61F 2002/3055* (2013.01); *A61F 2002/30168* (2013.01); *A61F 2002/30405* (2013.01); *A61F 2002/30494* (2013.01); *A61F 2002/30495* (2013.01); *A61F 2002/30507* (2013.01); *A61F 2002/30523* (2013.01); *A61F 2002/30556* (2013.01); *A61F 2002/30574* (2013.01); *A61F 2002/30593* (2013.01); *A61F 2002/30601* (2013.01); *A61F 2002/30841* (2013.01); *A61F 2002/30904* (2013.01); *A61F 2002/4627* (2013.01); *A61F 2002/4629* (2013.01)

(58) Field of Classification Search
 CPC .................................................. A61F 2/44–447
 See application file for complete search history.

(56) References Cited

U.S. PATENT DOCUMENTS 6,015,436 A 1/2000 Schönhöffer
6,200,348 B1 3/2001 Biedermann et al.
(Continued)

OTHER PUBLICATIONS

PowerPoint entitled "Competitive Designs", pp. 1-18.

*Primary Examiner* — Nicholas J Plionis
*Assistant Examiner* — Steven J Cotroneo
(74) *Attorney, Agent, or Firm* — Ronald A. Rudder; Olive Law Group, PLLC

(57) ABSTRACT

A spinal implant for placement between first and second vertebrae includes a housing having first and second axial end surfaces and a bore extending along an axis through the housing and between the end surfaces. A first projection extends at least partially about the axis and including a channel. A lift is slidably received in the bore and includes threads along its length. A collar is threadably engaged with the lift and extends into the channel on the housing such that the projection prevents axial movement of the collar relative to the housing. Rotation of the collar about the axis causes the lift to move axially relative to the collar and the housing for adjusting the height of the implant.

28 Claims, 27 Drawing Sheets

(56) References Cited

U.S. PATENT DOCUMENTS

| | | | |
|---|---|---|---|
| 6,524,341 B2 * | 2/2003 | Lang | A61F 2/44 623/17.15 |
| 6,752,832 B2 | 6/2004 | Neumann | |
| 7,641,693 B2 * | 1/2010 | Gutlin | A61F 2/44 623/17.15 |
| 7,819,920 B2 | 10/2010 | Assaker | |
| 7,824,445 B2 | 11/2010 | Biro et al. | |
| 7,887,594 B2 | 2/2011 | Berry et al. | |
| 8,182,537 B2 | 5/2012 | Refai et al. | |
| 8,197,546 B2 * | 6/2012 | Doubler | A61F 2/44 606/279 |
| 8,231,681 B2 | 7/2012 | Castleman et al. | |
| 8,241,363 B2 | 8/2012 | Sommerich et al. | |
| 8,273,126 B2 | 9/2012 | Lindner | |
| 8,282,683 B2 * | 10/2012 | McLaughlin | A61F 2/44 623/17.11 |
| 8,632,592 B2 | 1/2014 | Barrall | |
| 8,771,360 B2 | 7/2014 | Jimenez et al. | |
| 8,900,308 B2 | 12/2014 | Biedermann et al. | |
| 8,920,502 B1 | 12/2014 | Muhanna | |
| 9,301,850 B2 * | 4/2016 | McLaughlin | A61F 2/44 |
| 9,474,621 B2 * | 10/2016 | McLaughlin | A61F 2/44 |
| 2007/0191954 A1 * | 8/2007 | Hansell | A61F 2/442 623/17.15 |
| 2010/0249934 A1 | 9/2010 | Melkent | |
| 2011/0178598 A1 * | 7/2011 | Rhoda | A61F 2/44 623/17.16 |
| 2011/0218631 A1 * | 9/2011 | Woodburn, Sr. | A61F 2/442 623/17.16 |
| 2012/0226356 A1 | 9/2012 | Hirschl | |
| 2012/0265303 A1 * | 10/2012 | Refai | A61F 2/44 623/17.11 |
| 2013/0331943 A1 * | 12/2013 | Arnold | A61F 2/4455 623/17.15 |
| 2014/0142706 A1 * | 5/2014 | Hansell | A61F 2/4611 623/17.16 |
| 2016/0100955 A1 * | 4/2016 | Stinchfield | A61F 2/4465 623/17.15 |

\* cited by examiner

EXPANDABLE SPINAL CAGE ASSEMBLIES FOR SUPPORTING BONE STRUCTURES

RELATED APPLICATIONS

This application claims priority from U.S. Provisional Application Ser. Nos. 62/502,844, filed May 8, 2017 and 62/633,769, filed Feb. 22, 2018, the entirety of which are incorporated by reference herein.

TECHNICAL FIELD

The present disclosure relates to medical implants to support bone structures and, more specifically, relates to adjustable spinal cage assemblies for placement between adjacent vertebrae.

BACKGROUND

Several orthopedic procedures involve the removal of bone structures. For example, an interbody fusion procedure involves removing an intervertebral disc between vertebrae and placing a bone graft in the space between the vertebrae. In such procedures, a fusion cage is often placed in the interbody space to maintain foraminal height and decompression. A corpectomy is a surgical procedure where all or a portion of a vertebral body is removed to relieve pressure or decompress the spinal cord and nerves. A corpectomy cage is often used to fill the space created by the vertebrae removal.

Many such spinal cages are of fixed height or expandable. Fixed cages are manufactured in various heights so that one cage can be selected to best fit the cavity created by the removed vertebral body or disc. Alternatively, an expandable cage can be provided with an adjustable height to maintain spacing of the vertebrae above and below the removed vertebral or disc material.

SUMMARY

In one example, a spinal implant for placement between first and second vertebrae includes a housing having first and second axial end surfaces and a bore extending along an axis through the housing and between the end surfaces. A first projection extends at least partially about the axis and including a channel. A lift is slidably received in the bore and includes threads along its length. A collar is threadably engaged with the lift and extends into the channel on the housing such that the projection prevents axial movement of the collar relative to the housing. Rotation of the collar about the axis causes the lift to move axially relative to the collar and the housing for adjusting the height of the implant.

In another example, a spinal implant for placement between first and second vertebrae includes a housing having first and second axial end surfaces and a bore extending along an axis through the housing and between the end surfaces. A tapered projection extends from an end of the housing and includes a recess extending about the axis. A first adaptor has bone engaging structure formed thereon. A first retaining ring is provided on the first adaptor. The first retaining ring has an expanded condition allowing the first adaptor to be moved over the tapered projection on the housing and a collapsed condition locking the first adaptor to the housing. A lift is slidably received in the bore and includes threads along its length. A tapered projection extends from an end of the lift and includes a recess extending about the axis. A second adaptor has bone engaging structure formed thereon. A second retaining ring is provided on the second adaptor. The second retaining ring has an expanded condition allowing the second adaptor to be moved over the tapered projection on the lift and a collapsed condition locking the second adaptor to the lift. A collar is threadably engaged with the lift such that rotation of the collar about the axis causes the lift and second adaptor to move axially relative to the housing for adjusting the height of the implant.

Other objects and advantages and a fuller understanding of the invention will be had from the following detailed description and the accompanying drawings.

DETAILED DESCRIPTION

The present disclosure relates to medical implants to support bone structures and, more specifically, relates to adjustable spinal cage assemblies for placement between adjacent vertebrae. The spinal cage assembly can be used with, for example, portion of the cervical spine (C2-T1) or thoracolumbar spine (T1-L5) in skeletally mature patients for partial or total replacement of a diseased, damaged or unstable vertebral body due to tumor, osteomyelitis, trauma, e.g., fracture, or for reconstruction following corpectomy performed to achieve decompression of the spinal cord and neural tissues in degenerative disorders.

The spinal cage assemblies described and shown herein can be used with autograft or allogenic bone grafts comprised of cancellous and/or corticocancellous bone grafts as an adjacent to fusion. The spinal cage assembly can be used to restore spinal column integrity in the absence of fusion for a limited time in patients with advanced stage tumors involving the cervical, thoracic, and lumbar spine. Example spinal fixation systems that can be used in conjunction with the spinal cage assemblies described herein include posterior screw and rod systems and anterior plate systems. The spinal cage assemblies can be formed from a biocompatible material, such as titanium.

Figure 1:
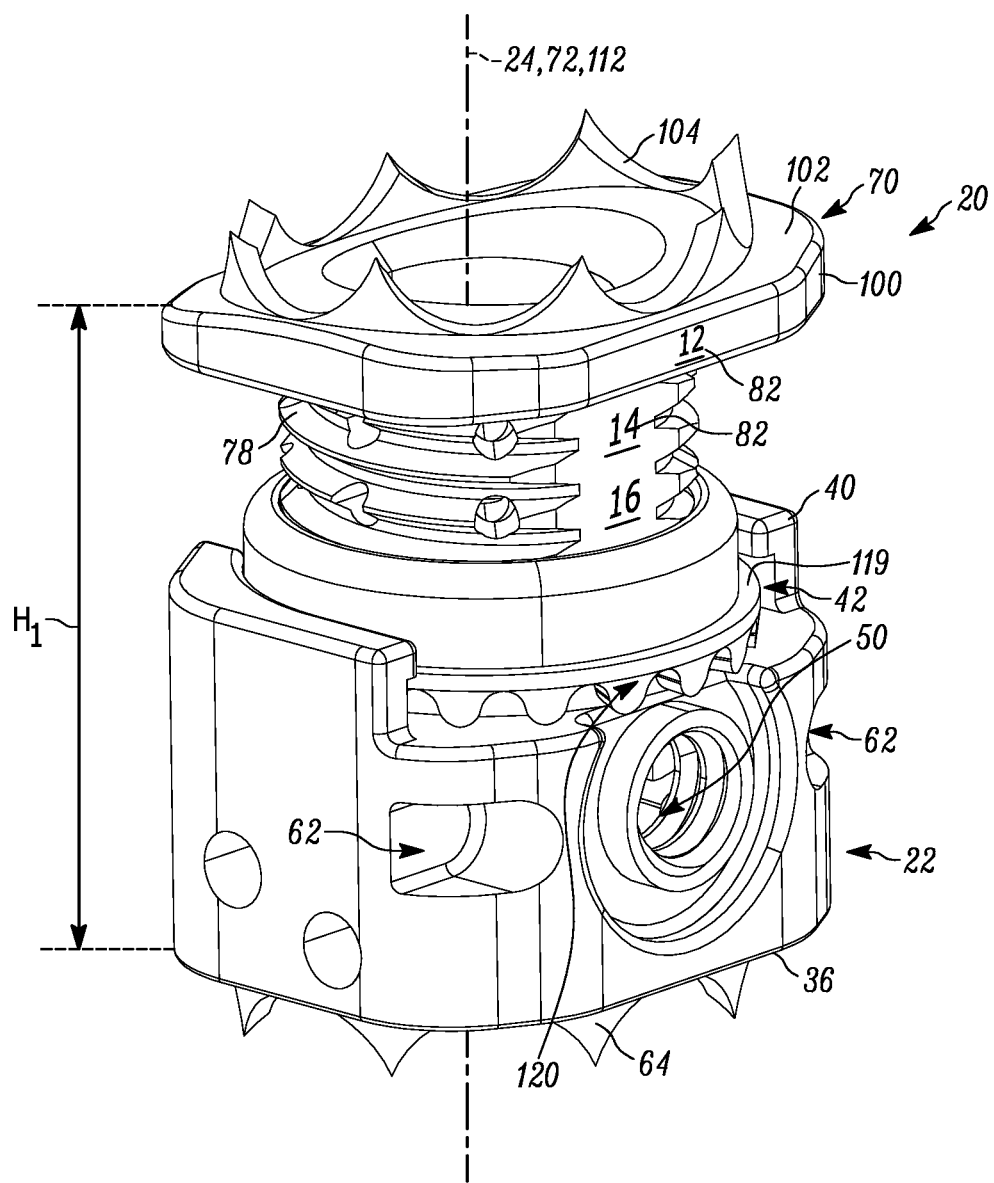
FIG. 1 illustrates an example spinal cage assembly.
Figure 2:
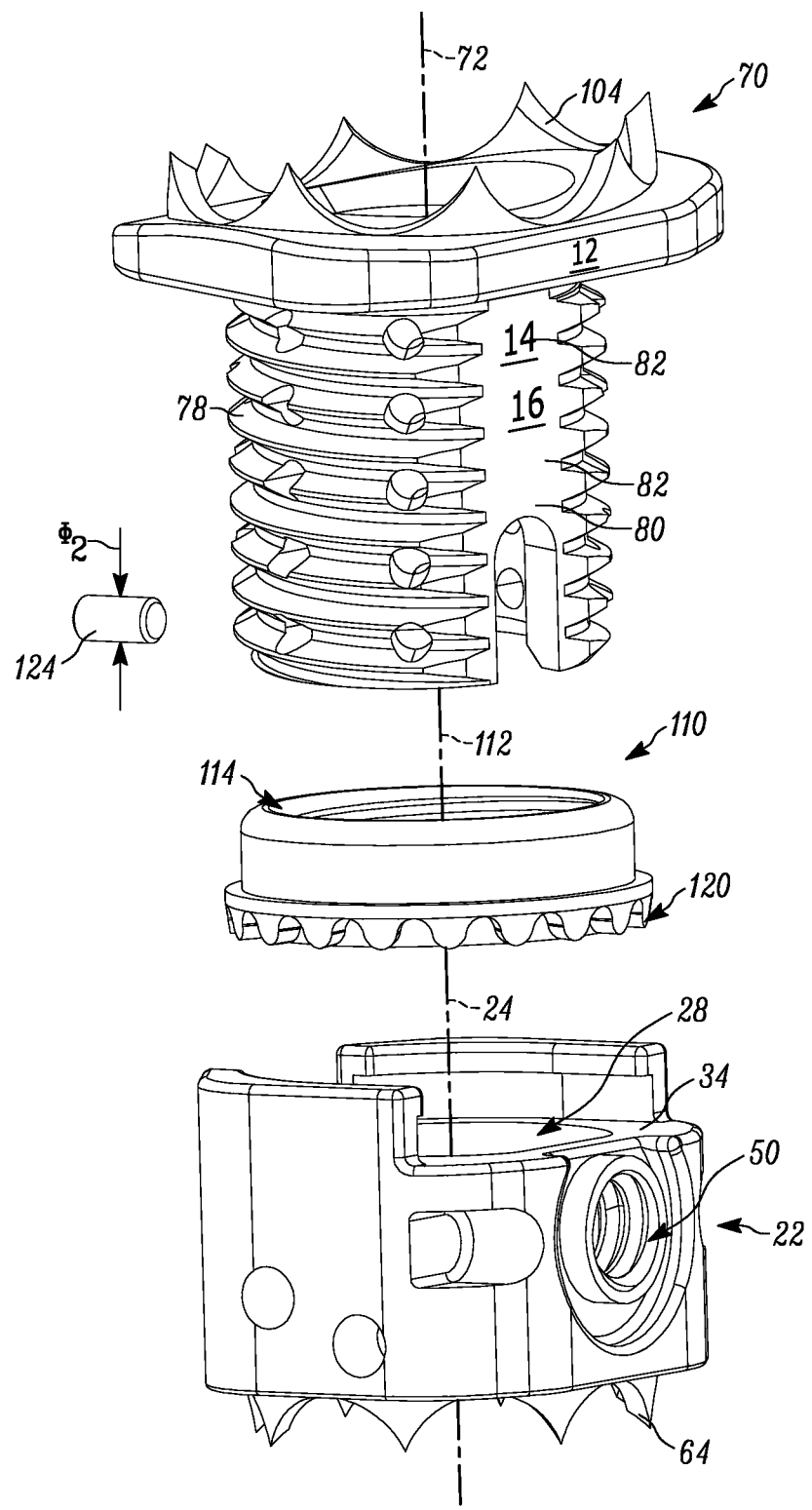
FIG. 2 is an exploded view of the spinal cage assembly of FIG. 1.
Figure 3A:
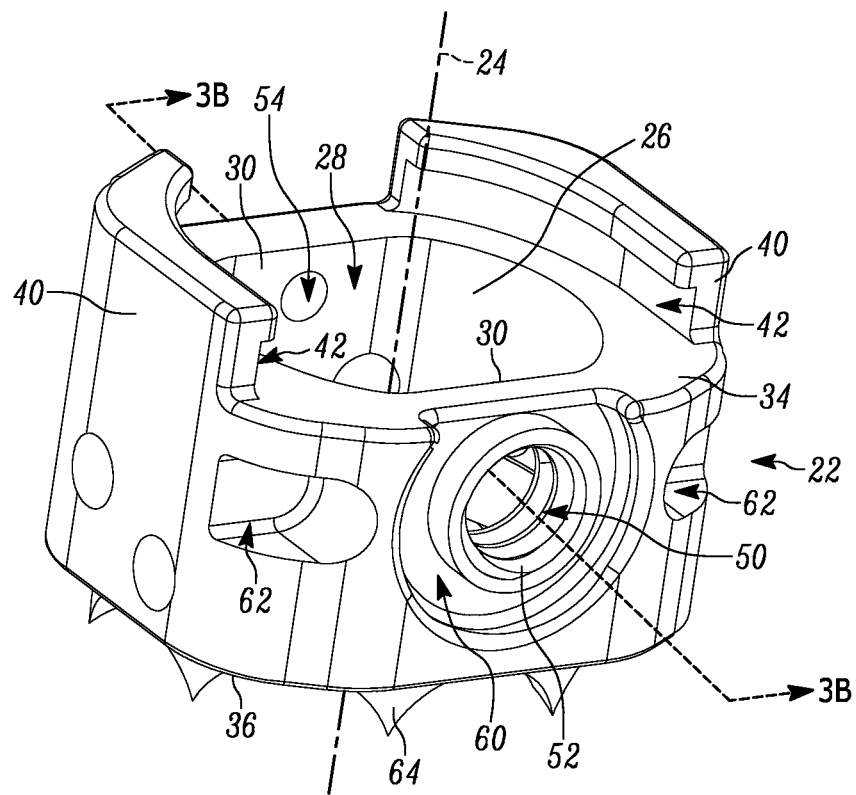
FIG. 3A is a front view of a housing of the spinal cage assembly of FIG. 1.
Figure 3B:
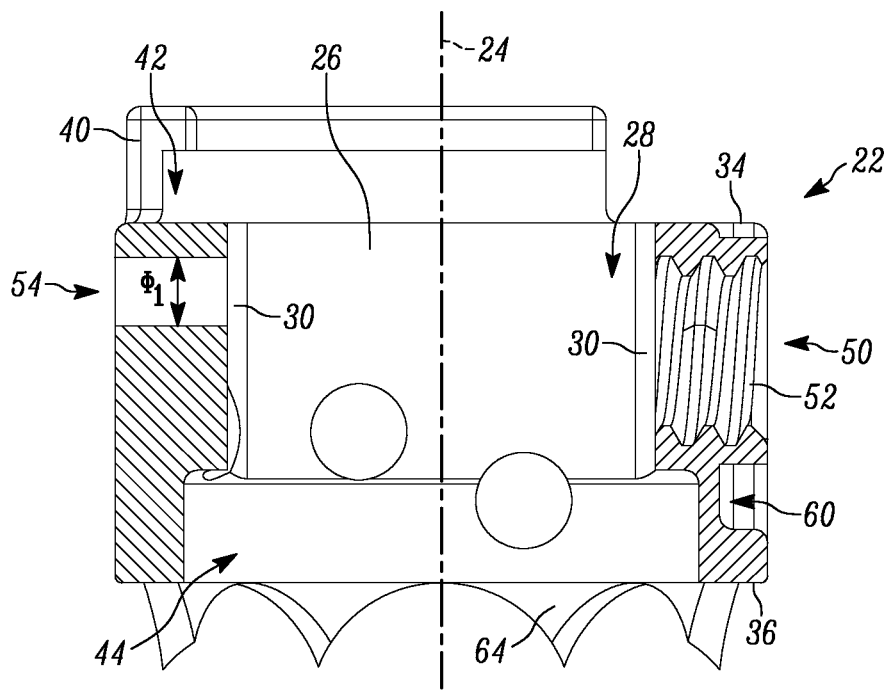
FIG. 3B is a section view of the housing of FIG. 3A taken along line 3B-3B.

An example expandable spinal cage assembly 20 is shown in FIGS. 1-2. The cage assembly 20 can be used as a cervical cage. The cage assembly 20 includes a housing 22, a lift 70, a collar 110, and a pin 124. Referring to FIGS. 3A-3B, the housing 22 is generally tubular and extends along an axis 24. An inner surface 26 defines an axial bore 28 extending along the length of the housing 22. The inner surface 26 includes planar portions 30 positioned on opposite sides of the axis 24. The planar portions 30 extend parallel to one another.

The housing 22 includes first and second axial end surfaces 34, 36 at opposite ends thereof. Projections 40 extend from the first end surface 34. Each projection 40 has an L-shaped cross-section defining a channel 42. The projections 40 are positioned on opposite sides of the axis 24. Bone engaging structure 64 extends from the second end surface 36. A countersink 44 extends from the second end surface 36 to the bore 28.

First and second passages 50, 54 extend radially through the housing 22 to the axial bore 28. Threads 52 are provided along the length of the first passage 50. A recess 60 formed in the housing 22 extends around the first passage 50. As shown, the recess 60 is circular. The second passage 54 has a diameter $\Phi_1$. Cavities 62 extend into the housing 22 on opposite sides of the recess 60 and are symmetrically arranged about the recess.

Figure 4A:
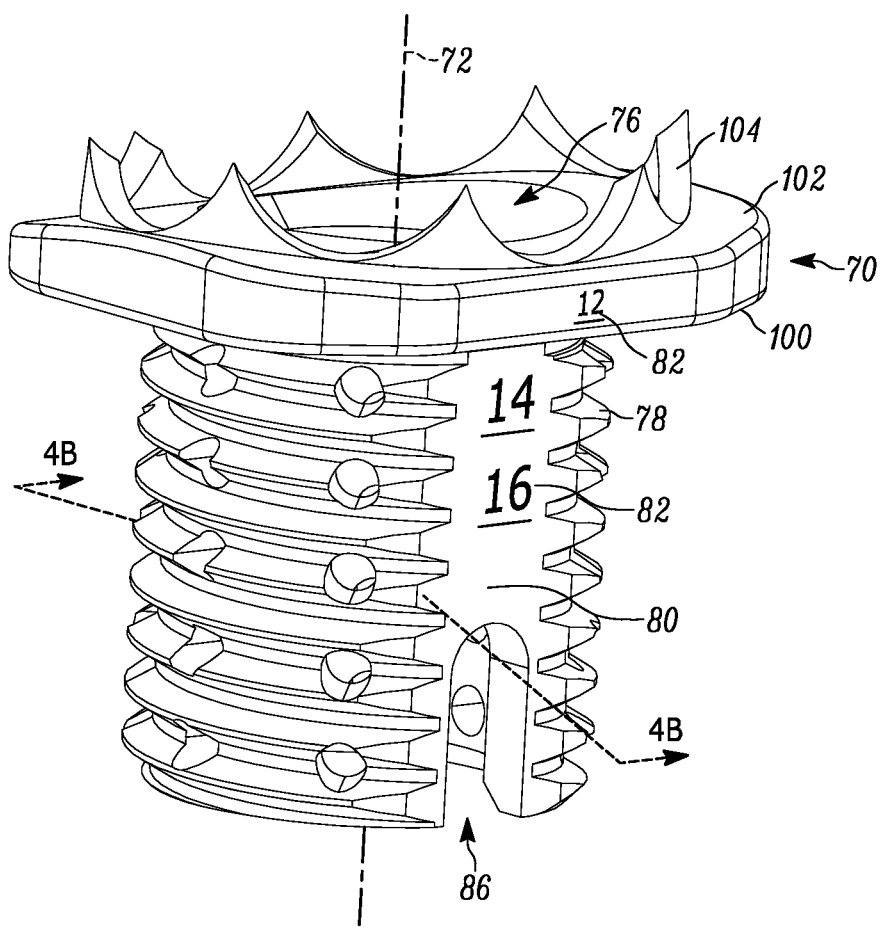
FIG. 4A is a front view of a lift of the spinal cage assembly of FIG. 1.
Figure 4B:
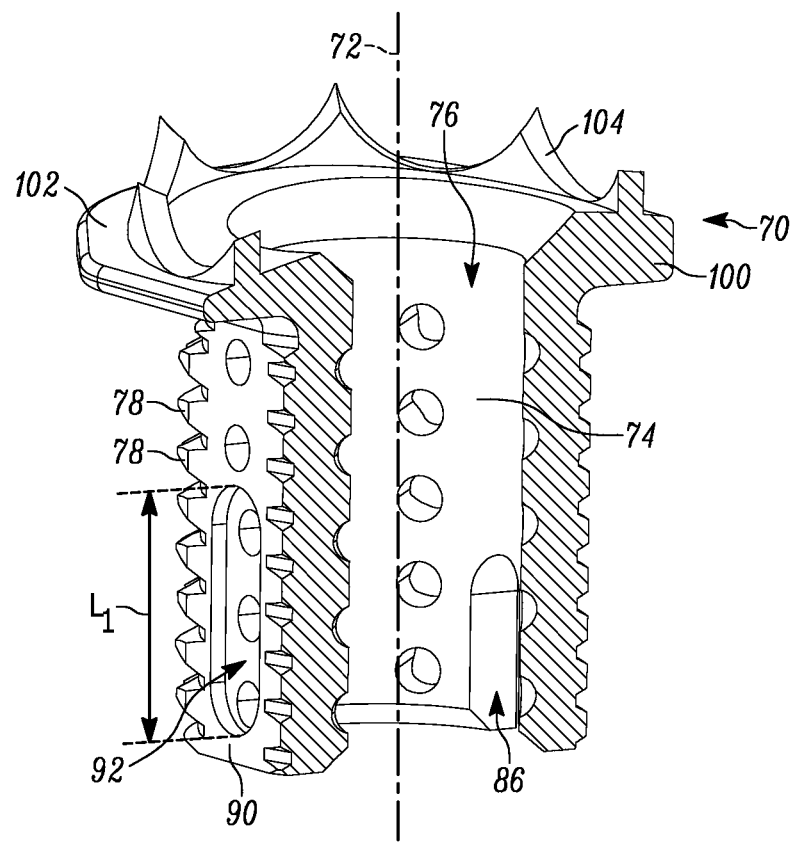
FIG. 4B is a section view of the lift of FIG. 4A taken along line 4B-4B.

Referring to FIGS. 4A-4B, the lift 70 is generally tubular and extends along an axis 72. An inner surface 74 defines an axial bore 76 extending the entire length of the lift 70. The exterior of the lift 70 includes threads 78. Planar surfaces 80, 90 are formed in the threads 78 on opposite sides of the axis 72. Each planar surface 80, 90 extends the axial length of the threads 78. Indicia 82 are provided along the planar surface 80. In one example, the indicia 82 are units of measurement in millimeters and are indicative of the overall height $H_1$ of the cage assembly 20 (see FIG. 1).

A passage 86 extends radially through the planar surface 80 to the bore 76. A recess 92 extends into the planar surface 90 and terminates prior to the bore 76. The recess 92 has a length $L_1$ and is oval-shaped.

A flange 100 extends radially outward from the lift 70 and encircles the bore 76. The flange 100 includes an axial end surface 102. Bone engaging structure 104 extends from the end surface 102. Indicia 82 are provided on the flange 100 and are axially aligned with the indicia 82 on the planar surface 80.

Figure 5:
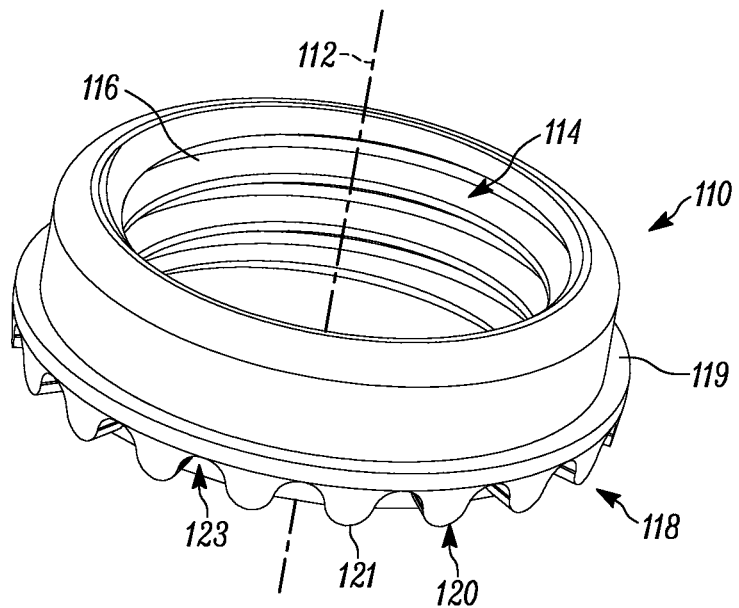
FIG. 5 is a front view of a collar of the spinal cage assembly of FIG. 1.

As shown in FIG. 5, the collar 110 is ring-shaped and extends along an axis 112. A threaded inner surface 116 of the collar 110 defines an axial bore 114 extending the length of the collar. An end 118 of the collar 110 includes a flange 119 extending radially outward from the collar. A gearwheel 120 is provided on the flange 119 and encircles the axis 112. The gearwheel 120 includes projections 121 and recesses 123 arranged in an alternating manner around the collar 110 in an endless loop.

When the cage assembly 20 is assembled (see FIGS. 1-2), the lift 70 extends within the bore 28 of the housing 22 and the bore 114 in the collar 110 and is threadably engaged therewith. More specifically, the lift 70 extends through the bore 114 in the collar 110 and the threads 78 on the lift engage the threads 116 on the collar. The flange 119 of the collar 110 extends into the channels 42 in the projections 40 of the housing 22. The gearwheel 120 rests on the end surface 34 of the housing 22. This configuration allows the collar 110 to rotate relative to the housing 22 but relative axial movement between the collar and housing is prevented.

The planar surfaces 80, 90 on the lift 70 are radially aligned with and slide along the planar portions 30 of the inner surface 26 of the housing 22. Consequently, the lift 70 is axially moveable relative to the housing 22 but relative rotational movement between the lift and the housing is prevented.

The indicia 82 are aligned with the first radial passage 50 in the housing 22. The second radial passage 54 is aligned with the recess 92 in the lift 70. The pin 124 (see FIG. 2)—having a diameter $\Phi_2$ substantially equal to the diameter $\Phi_1$ of the second radial passage 54—extends through the second radial passage and into the recess 92. The pin 124 can be staked to the housing 22 or otherwise rigidly fixed in place within the second radial passage 54. The distance between the end surface 102 of the flange 100 and the end surface 36 of the housing 22 defines the height $H_1$ of the cage assembly 20.

Figure 6A:
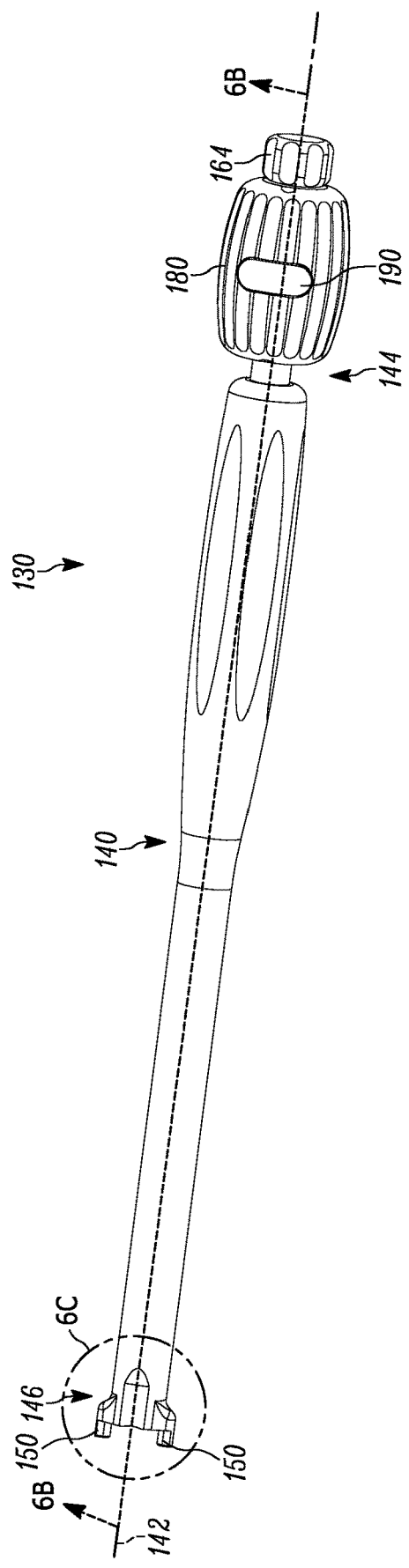
FIGS. 6A-6C are views of a tool for adjusting the spinal cage assembly of FIG. 1.
Figure 6B:
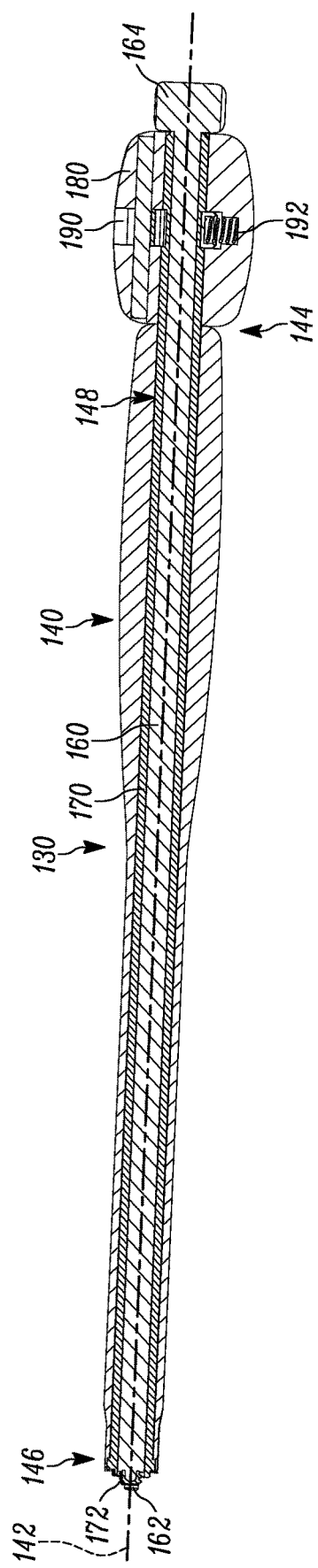
Figure 6C:
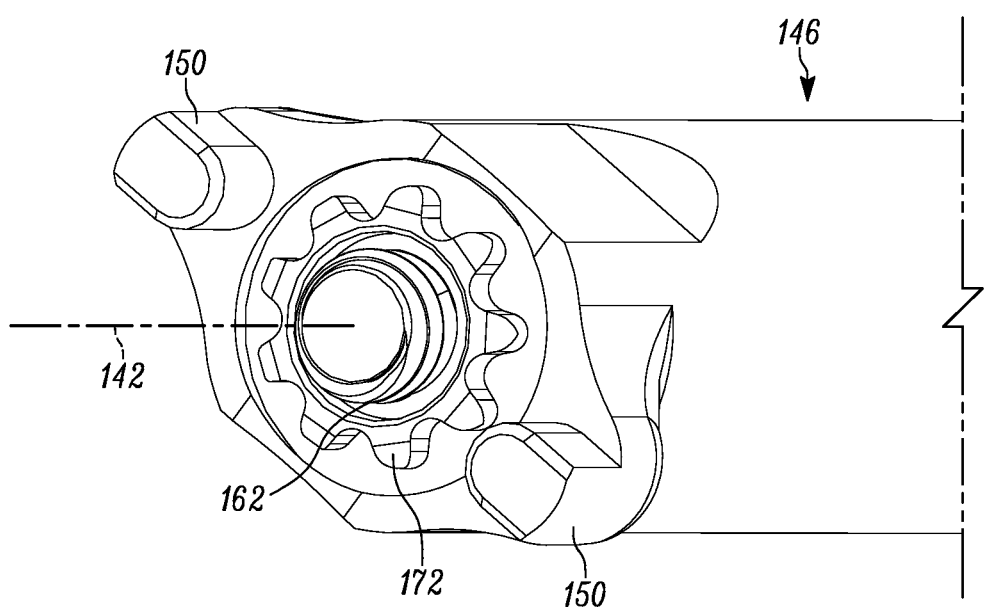

A tool 130 is used to adjust the height $H_1$ of the cage assembly 20. As shown in FIGS. 6A-6C, the tool 130 includes a body 140 extending longitudinally along an axis 142 from a first end 144 to a second end 146. A passage 148 extends the entire length of the body 140. A pair of projections 150 is provided on the second end 146. The projections 150 are symmetrically arranged about the axis 142.

A shaft 160 is provided within the passage 148 of the body 140. A threaded end 162 of the shaft 160 is axially exposed through the second end 146 of the body 140. A handle 164 is provided on the opposite end of the shaft 160. A sleeve 170 is positioned within the passage 148 of the body 140 and is located radially between the shaft 160 and the body. An end of the sleeve 170 adjacent the second end 146 of the body 140 includes a gearwheel 172 similar in construction to the gearwheel 120 on the collar 110.

A handle 180 is secured to the sleeve 170 and provided between the first end 144 of the housing 140 and the handle 164 on the shaft 160. Both the sleeve 170 and the shaft 160 extend through the handle 180. The sleeve 170 is secured to the handle 180 for rotation therewith about the axis 142 and relative to the body 140 and the shaft 160. A spring 192 provided within the handle 180 biases the shaft 160 into a locked condition with the handle. A button 190 connected to the shaft 160 can be depressed to release the spring 192 bias and decouple the shaft from the handle 180 to allow for disassembly of the tool 130.

Figure 7A:
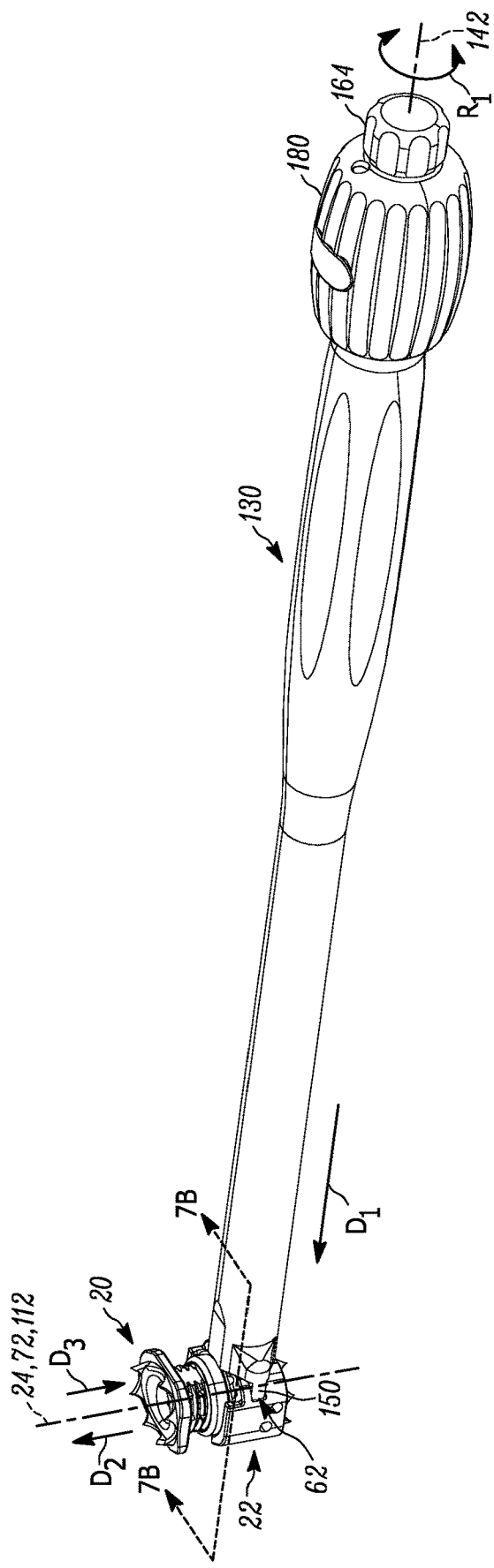
FIGS. 7A-7B are views illustrating operation of the tool of FIGS. 6A-6C.
Figure 7B:
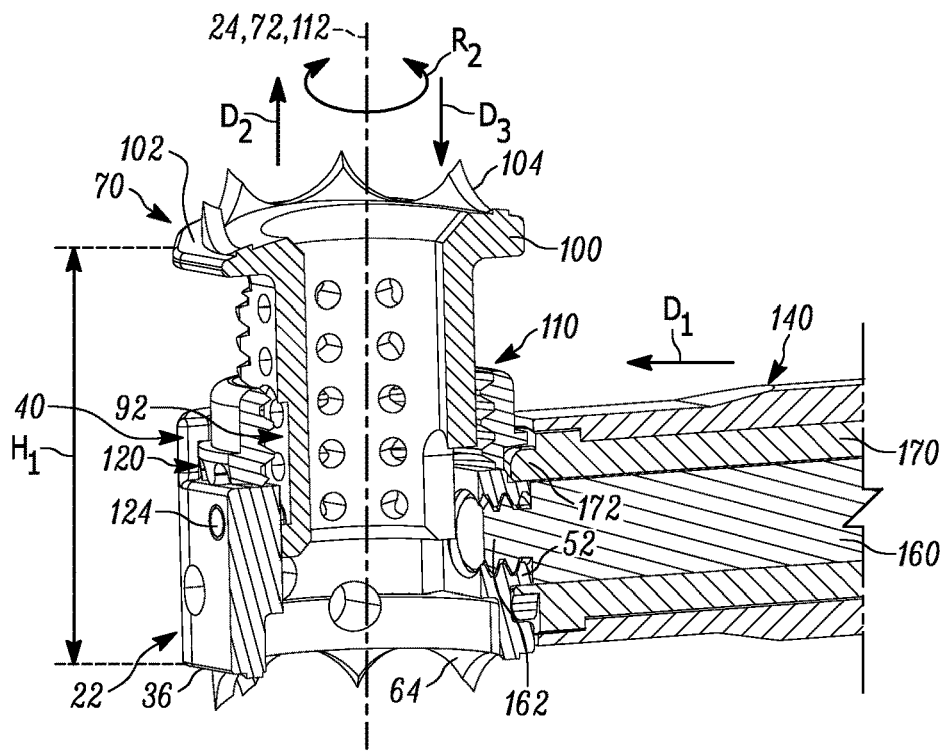
Figure 8:
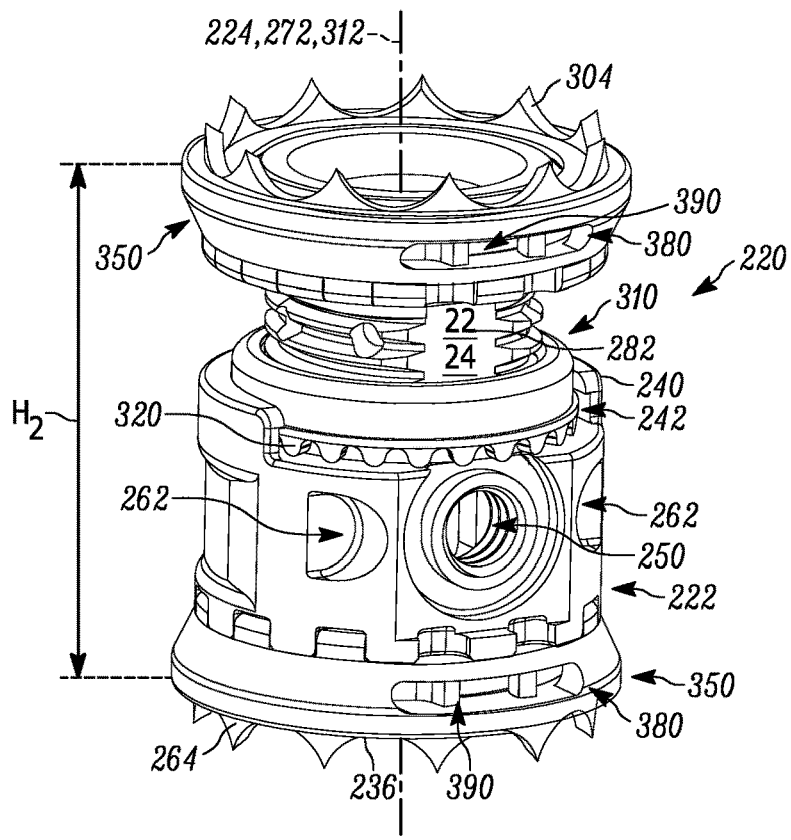
FIG. 8 illustrates another example spinal cage assembly.
Figure 9:
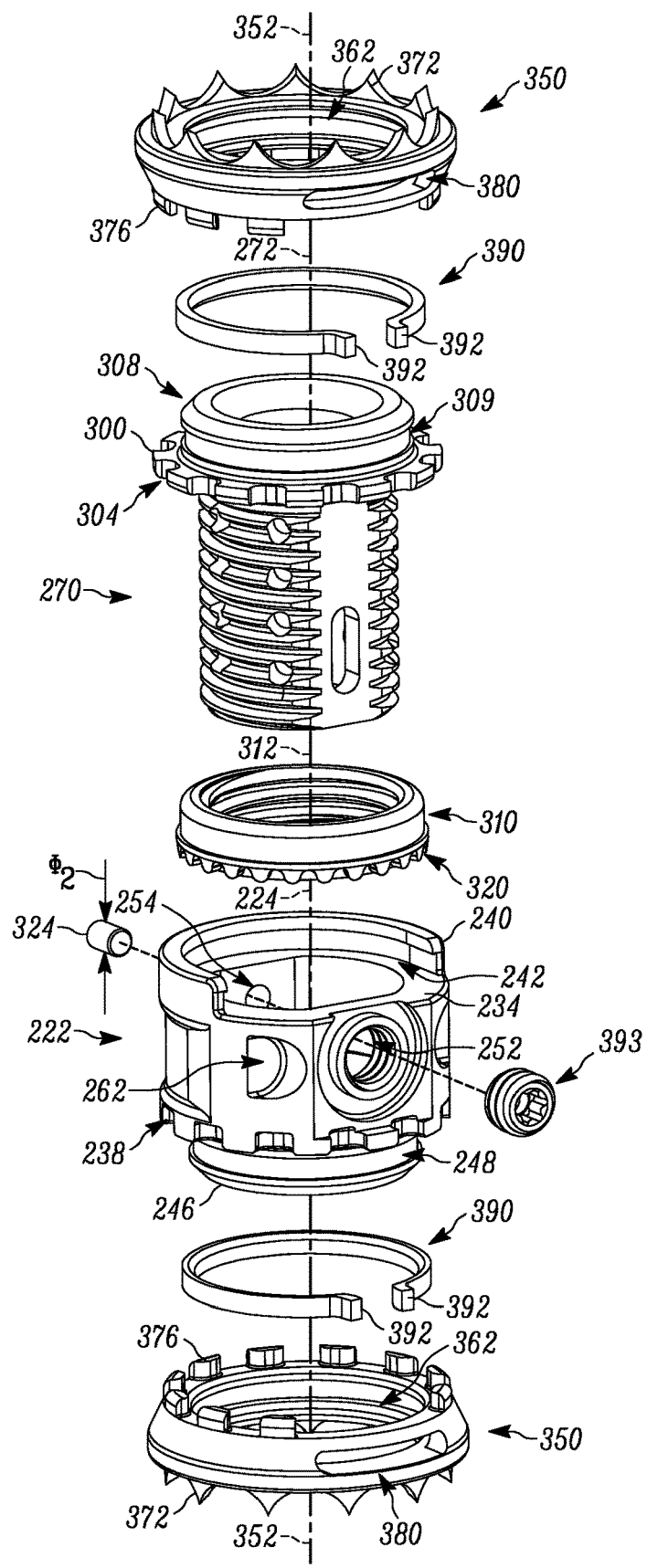
FIG. 9 is an exploded view of the spinal cage assembly of FIG. 8.

In use, the projections 150 on the second end 146 of the body 140 are inserted into the cavities 62 in the housing 22 to prevent relative movement between the body and the cage assembly 20 (see FIGS. 7A-7B). This also aligns the threaded end 162 of the shaft 160 with the threads 52 in the housing 22. At this point, the assembled cage assembly 20 has an initial height $H_1$ less than the intervertebral spacing. The user then maneuvers the assembled cage assembly 20 into place between adjacent vertebrae along the spine (not shown).

Once the cage assembly 20 is properly positioned, the handle 164 is rotated clockwise about the axis 142 in the manner $R_1$, which rotates the threaded end 162 of the shaft 160 in the clockwise manner $R_1$ relative to the housing 140 and sleeve 170. This causes the threads 162 to engage the threads 52 and advance the shaft 160 along the axis 142 in the direction $D_1$ relative to the fixed body 140. The threads 162 advance into the threads 52 in the direction $D_1$ until the shaft 160 bottoms out against the housing 22 exterior. This bottoming out radially aligns and meshes the gearwheel 172 on the sleeve 170 with the gearwheel 120 on the collar 110.

At this point, rotating the handle 180 about the axis 142 in the manner $R_1$ causes the sleeve 170 to rotate about the axis 142 relative to the fixed body 140 and shaft 160. Rotating the sleeve 170 causes the gearwheel 172 to rotate the meshed gearwheel 120 on the collar 110 about the axis 112 in the manner $R_2$. In other words, rotating the handle 180 causes the collar 110 to rotate within the channels 42 in the housing 22 relative to the housing.

As noted, the collar 110 is threadably engaged with the lift 70 and prevented from moving axially by the projection 40. Consequently, rotating the collar 110 in the manner $R_2$ causes the lift 70 to move axially relative to the collar and the housing 22. To this end, rotating the collar 110 in the counterclockwise manner $R_2$ causes the lift 70 to move in the direction $D_2$, thereby increasing the height $H_1$ of the cage assembly 20. On the other hand, rotating the collar 110 in the clockwise manner $R_2$ causes the lift 70 to move in the direction $D_3$, thereby decreasing the height $H_1$ of the cage assembly 20. Rotating the handle 180 in the clockwise manner $R_1$ therefore increases the height $H_1$ of the cage assembly 20. Rotating the handle 180 in the counterclockwise manner $R_1$ therefore decreases the height $H_1$ of the cage assembly 20.

In either case, the user operating the handle 180 can rely on the indicia 82 along the lift 70 to adjust the height $H_1$ of the cage assembly 20 until a desired value is reached. As the height $H_1$ increases, the bone engaging structures 64, 104 move into engagement with the adjacent vertebrae and apply outward compressive forces against the vertebrae to help hold the cage assembly 20 in place.

It will be appreciated that the length $L_1$ of the recess 92 in the lift 70 dictates the range of heights $H_1$ over which the cage assembly 20 can be adjusted. To this end, the pin 124 bottoms out at the end of the recess 92 to prevent additional axial movement of the lift 70 beyond a predetermined amount when the cage assembly 20 reaches the longest possible height $H_1$.

Once the cage assembly 20 has the desired height $H_1$, a lock screw (not shown) can be threaded into the threads 52 to prevent additional adjustment of the cage assembly 20. To this end, the handle 164 is rotated in the counterclockwise manner $R_1$ to unthread the threads 162 from the threads 52 in the housing 22. After the threads 52, 162 are released from one another, the user pulls the shaft 160 in a direction opposite the direction $D_1$ to remove the shaft from the sleeve 170. The empty sleeve 170 can then be used as a guide for directing the lock screw to the threads 52 in the cage assemble 20.

After the lock screw is in place, the user pulls the body 140 away from the cage assembly 20 and along the axis 142 in a direction opposite the direction $D_1$ to release the tool 130 completely from the cage assembly. Alternatively, the lock screw can be threaded into the threads 52 once the tool 130 is removed entirely from the cage assembly.

Another example expandable spinal cage assembly 220 is shown in FIGS. 8-13. The cage assembly 220 can be used as a thoracic and lumbar cage. The cage assembly 220 includes a housing 222, a lift 270, a collar 310, a pin 324, and one or more adaptors 350. Referring to FIGS. 10A-10B, the housing 222 is generally tubular and extends along an axis 224. An inner surface 226 defines an axial bore 228 extending along the length of the housing 222. The inner surface 226 includes planar portions 230 positioned on opposite sides of the axis 224. The planar portions 230 extend parallel to one another.

The housing 222 includes first and second axial end surfaces 234, 236 at opposite ends thereof. Projections 240 extend from the first end surface 234. Each projection 240 has an L-shaped cross-section defining a channel 242. The projections 240 are positioned on opposite sides of the axis 224.

Figure 10A:
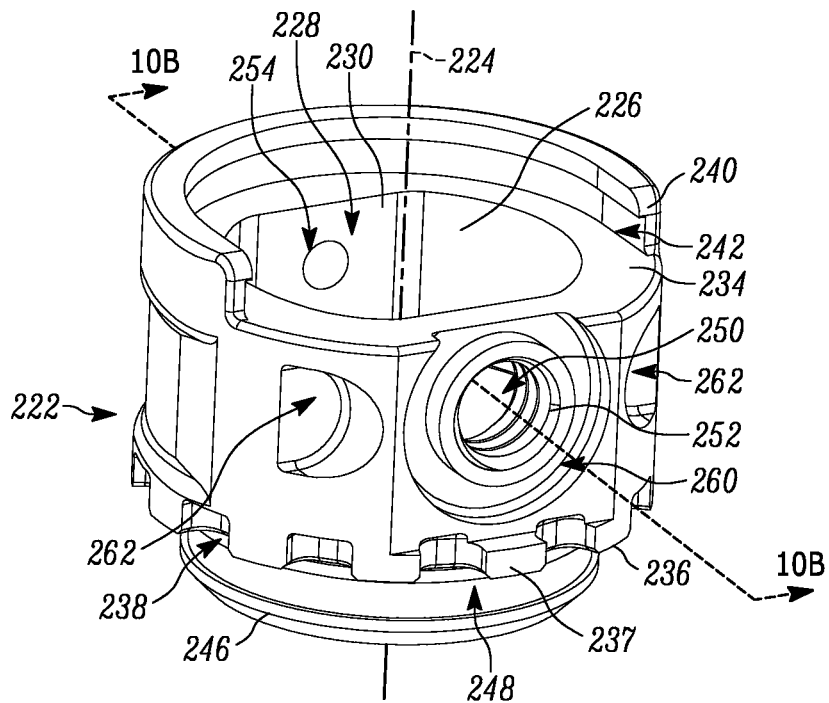
FIG. 10A is a front view of a housing of the spinal cage assembly of FIG. 8.
Figure 10B:
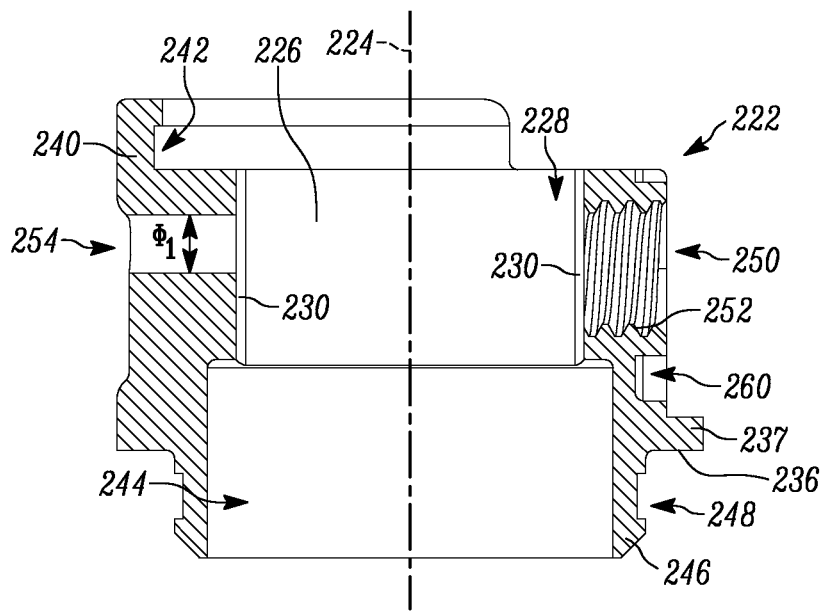
FIG. 10B is a section view of the housing of FIG. 10A taken along line 10B-10B.
Figure 10C:
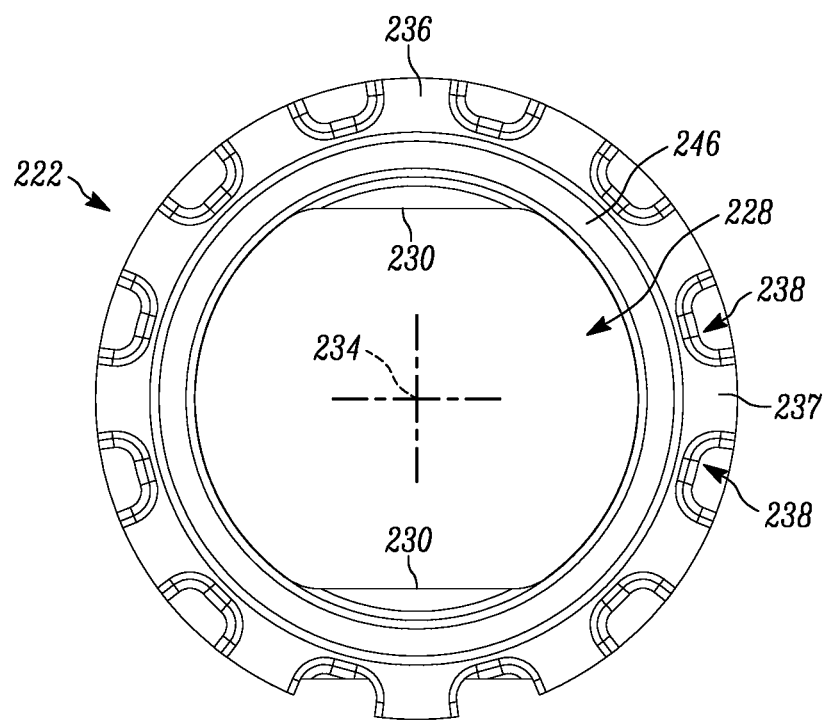
FIG. 10C is a bottom view of the housing of FIG. 10A.

A flange 237 extends radially outward from the housing 222 and defines the second end surface 236 (see also FIG. 10C). Recesses 238 formed in the flange 237 extend toward the axis 224 and can collectively encircle the axis. The recesses 238 can be arranged in a symmetric pattern (as shown) or an asymmetric pattern (not shown) about the axis 224. An annular projection 246 extends axially away from the flange 237. A recess 248 is formed in the projection 246 and encircles the axis 224. The leading end of the projection 246 can be tapered or frustoconical. A countersink 244 extends from the leading end of the projection 246 to the bore 228.

First and second passages 250, 254 extend radially through the housing 222 to the axial bore 228. Threads 252 are provided along the length of the first passage 250. A recess 260 formed in the housing 222 extends around the first passage 250. As shown, the recess 260 is circular. The second passage 254 has the diameter $\Phi_1$. Cavities 262 extend into the housing 222 on opposite sides of the recess 260 and are symmetrically arranged about the recess.

Figure 11A:
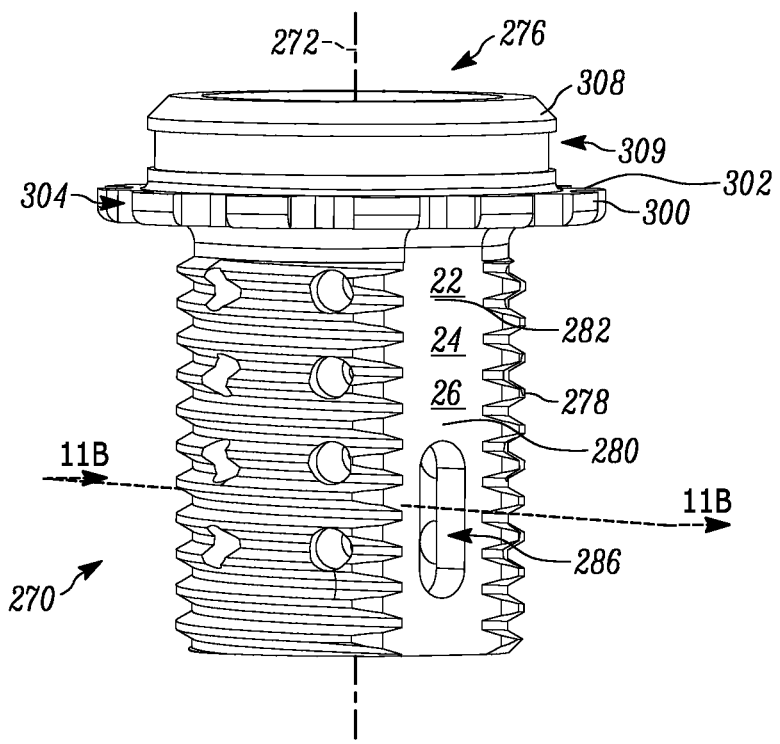
FIG. 11A is a front view of a lift of the spinal cage assembly of FIG. 8.
Figure 11B:
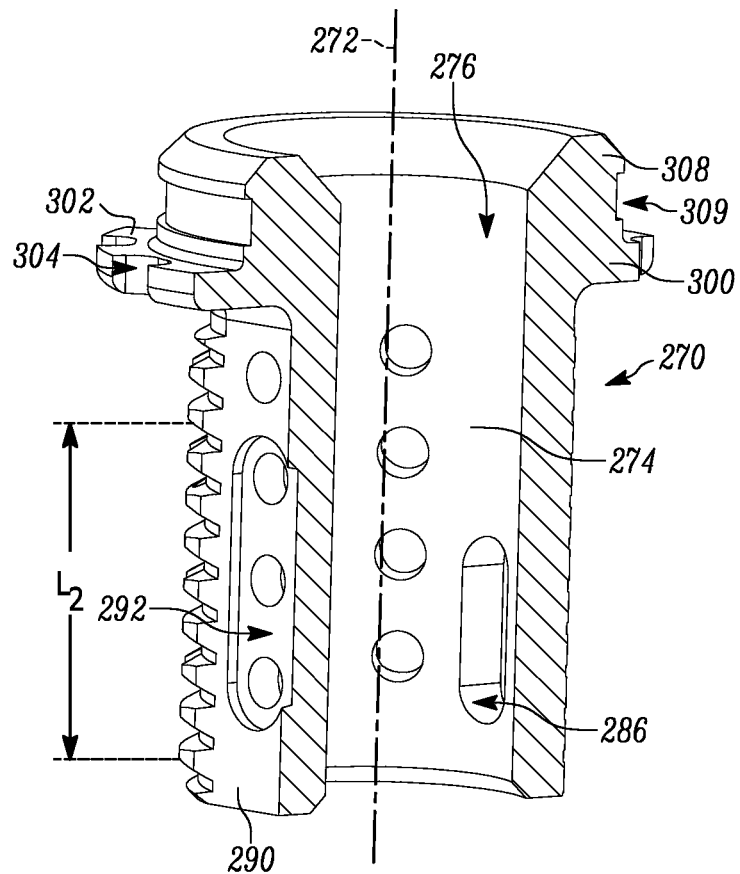
FIG. 11B is a section view of the lift of FIG. 11A taken along line 11B-11B.

Referring to FIGS. 11A-11B, the lift 270 is generally tubular and extends along an axis 272. An inner surface 274 defines an axial bore 276 extending the entire length of the lift 270. The exterior of the lift 270 includes threads 278. Planar surfaces 280, 290 are formed in the threads 278 on opposite sides of the axis 272. Each planar surface 280, 290 extends the axial length of the threads 278. Indicia 282 are provided along the planar surface 280. In one example, the indicia 282 are units of measurement in millimeters and are indicative of the overall height H₂ of the cage assembly 220 (see FIG. 8).

A passage 286 extends radially through the planar surface 280 to the bore 276. A recess 292 extends into the planar surface 290 and terminates prior to the bore 276. The recess 292 has a length L₂ and is oval-shaped.

A flange 300 extends radially outward from the lift 270 and encircles the bore 276. The flange 300 includes an axial end surface 302. Recesses 304 formed in the flange 300 extend toward the axis 272 and can collectively encircle the axis. The recesses 304 can be arranged in a symmetric pattern (as shown) or an asymmetric pattern (not shown) about the axis 272. An annular projection 308 extends from the axial end surface 302 axially away from the flange 300. An annular recess 309 is formed in the projection 308 and encircles the axis 272. The recess 309 is sized and shaped similar to the recess 248 in the housing 222. The leading end of the projection 308 can be tapered. That said, the flange 300 and projection 308 can have the same configuration as the flange 237 and projection 246 on the housing 222.

Figure 12:
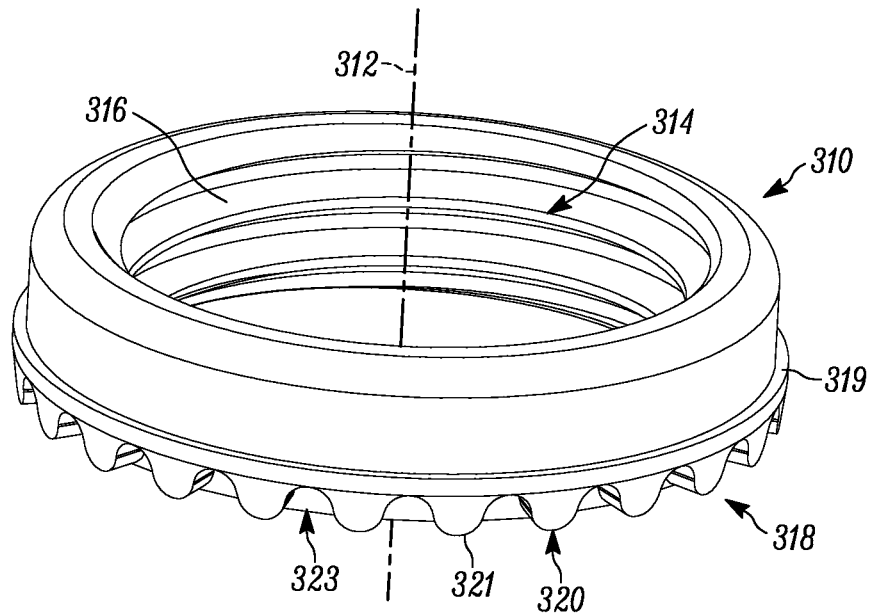
FIG. 12 is a front view of a collar of the spinal cage assembly of FIG. 8.

As shown in FIG. 12, the collar 310 is ring-shaped and extends along an axis 312. A threaded inner surface 316 of the collar 310 defines an axial bore 314 extending the length of the collar. An end 318 of the collar 310 includes a flange 319 extending radially outward from the collar. A gearwheel 320 is provided on the flange 319 and encircles the axis 312. The gearwheel 320 includes projections 321 and recesses 323 arranged in an alternating manner around the collar 310 in an endless loop.

Figure 13:
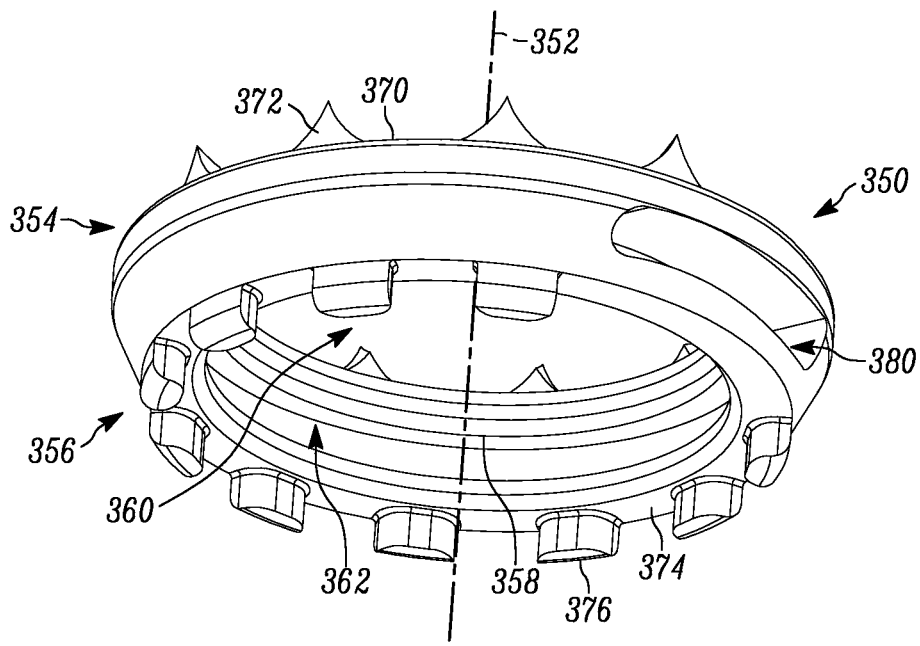
FIG. 13 is a view of an adapter of the spinal cage assembly of FIG. 8.
Figure 14:
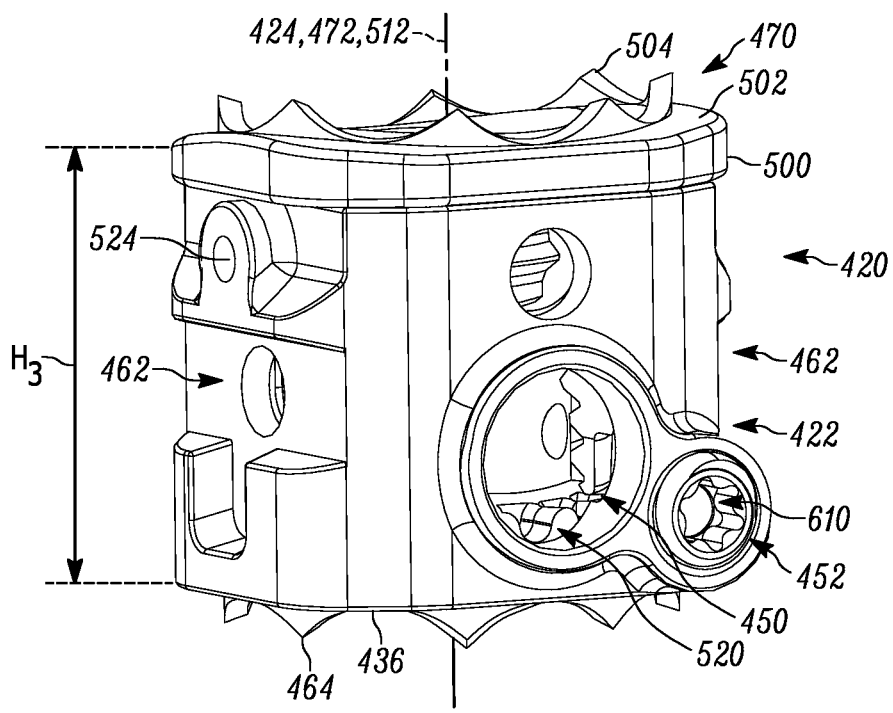
FIG. 14 illustrates yet another example spinal cage assembly.

Referring to FIG. 13, the adaptor 350 is ring-shaped and extends along an axis 352 from a first end 354 to a second end 356. An inner surface 358 defines an axial bore 360 extending along the length of the adaptor 350. An annular recess 362 extends along the inner surface 358 and encircles the axis 352. The recess 362 is sized and shaped similar to the recesses 248, 309 in the housing 222 and lift 270, respectively.

Bone engaging structure 372 extends from an axial end surface 370 at the first end 354. Spaced-apart projections 376 extend from an axial end surface 374 at the second end 356. The size, shape, and pattern of the projections 376 on the adaptor 350 corresponds with the size, shape, and pattern of the recesses 238 on the housing 222 as well as the size, shape, and pattern of the recesses 304 on the lift 270. A radial passage 380 extends through the adaptor 350 to the bore 360. The radial passage is axially aligned with the recess 362 along the inner surface 358 of the adaptor 350.

When the cage assembly 220 is assembled (see FIGS. 8-9), the lift 270 extends within the bore 228 of the housing 222 and the bore 314 in the collar 310 and is threadably engaged therewith. More specifically, the lift 270 extends through the bore 314 in the collar 310 and the threads 278 on the lift engage the threads 316 on the collar. The flange 319 of the collar 310 extends into the channels 242 in the projections 240 of the housing 222. The gearwheel 320 rests on the end surface 234 of the housing 222. This configuration allows the collar 310 to rotate relative to the housing 222 but relative axial movement between the collar and housing is prevented.

The planar surfaces 280, 290 on the lift 270 are radially aligned with and slide along the planar portions 230 of the inner surface 226 of the housing 222. Consequently, the lift 270 is axially moveable relative to the housing 222 but relative rotational movement between the lift and the housing is prevented.

The indicia 282 are aligned with the first radial passage 250 in the housing 222. The second radial passage 254 is aligned with the recess 292 in the lift 270. The pin 324 (see FIG. 9) having the diameter Φ₂ extends through the second radial passage 254 and into the recess 292. The pin 324 can be staked to the housing 222 or otherwise rigidly fixed in place within the second radial passage 254. The distance between the axial extent of the projection 308 on the lift 270 and the axial extent of the projection 246 on the housing 222 defines the height H₂ of the cage assembly 220.

The adaptors 350 are secured to the axial end of the housing 222 and lift 270 to provide the bone engaging structure thereto. To this end, resilient retaining rings 390 are provided in the recess 362 in each adaptor 350. The retaining rings 390 are positioned such that ends 392 thereof extend into the radial passage 380 of the adaptor 350.

To install one of the adaptors 350 on the housing 222, the axes 224, 352 are aligned with one another and the bone engaging structure 372 faces/extends away from the housing 222. The adaptor 350 is moved towards the housing 222 until the projection 246 on the housing enters the axial bore 360. Since the leading end of the projection 246 is tapered, when the projection engages the retaining ring 390 the ends 392 thereof are automatically forced apart from one another within the radial passage 380 to expand the retaining ring within the recess 362.

This allows the adaptor 350 to be inserted over the projection 246 until the projections 376 interdigitate with the recesses 238 on the flange 237. The ends 392 automatically move towards one another once the retaining ring 390 reaches the recess 248 and is no longer engaged by the leading end of the projection 246. This secures the retaining ring 390 within the recesses 248, 362 and prevents removal of the adaptor 350 from the housing 222 until/unless the ends 392 are again moved apart from one another.

To install the other adaptor 350 on the lift 270, the axes 272, 352 are aligned with one another and the bone engaging structure 372 faces/extends away from the lift 270. The adaptor 350 is moved towards the lift 270 until the projection 308 on the lift 270 enters the axial bore 360. Since the leading end of the projection 308 is tapered, when the projection engages the retaining ring 390 the ends 392 thereof are automatically forced apart from one another within the radial passage 380 to expand the retaining ring within the recess 362.

This allows the adaptor 350 to be inserted over the projection 308 until the projections 376 interdigitate with the recesses 304 on the flange 300. The ends 392 automatically move towards one another once the retaining ring 390 reaches the recess 309 and is no longer engaged by the leading end of the projection 308. This secures the retaining ring 390 within the recesses 309, 362 and prevents removal of the adaptor 350 from the lift 370 until/unless the ends 392 are again moved apart from one another by a tool inserted into the radial passage 380.

Once the spinal cage assembly 220 is assembled, the tool 130 is used to adjust the height H₂ of the spinal cage assembly 220 in the same manner as shown and described above with the spinal cage assembly 20. Since the cage assemblies 20, 220 are intended for implantation into different portions of the spine, it will be appreciated that the ranges for the heights H₁, H₂ can vary, overlap or be discrete from one another. Moreover, it will be appreciated that the tools used to install the respective cage assemblies 20, 220 can be sized differently but otherwise identical. In any case, once the tool 130 is removed from the cage assembly 220 a lock screw 393 (see FIG. 8) can be threaded into the threads 252 to prevent additional adjustment of the cage assembly 220. The lock screw 393 can have a splined, hexalobe, etc. tool receiving profile.

Another example expandable spinal cage assembly 420 is shown in FIGS. 14-18B. The spinal cage assembly 420 can be used as a cervical cage, thoracic cage or lumbar cage. The cage assembly 420 includes a housing 422, a lift 470, a collar 510, a pin 524, and a locking device 610. Referring to FIGS. 16A-16C, the housing 422 is generally tubular and extends along an axis 424. An inner surface 426 defines an axial bore 428 extending along the length of the housing 422. The inner surface 426 includes four planar portions 430 positioned on opposite sides of the axis 424. Diametrically opposed planar portions 430 extend parallel to one another.

The housing 422 includes first and second axial end surfaces 434, 436 at opposite ends thereof. Bone engaging structure 464 extends from the second end surface 436. An annular projection 437 extends radially inward from the inner surface 426 adjacent the second end surface 434. The projection 437 defines an inner surface 438 within the bore 428 positioned between the end surfaces 434, 436. The projection 437 also defines an annular channel 440 that encircles the axis 424 and extends around a portion of the bore 428.

Passages 450, 452, 454 extend through the housing 422 to the axial bore 428. The passage 450 extends radially and has a smooth, circular cross-section. The passage 452 includes a threaded portion 453 and an unthreaded portion 455. The unthreaded portion 455 intersects the inner surface 438. The passage 454 extends radially and has the diameter $\Phi_1$ (not shown). A countersink 457 having a diameter $\Phi_3$ larger than the diameter $\Phi_1$ is provided at an end of the radial passage 454 adjacent the inner surface 426.

A bead 449 encircles both passages 450, 452. Cavities 462 extend into the housing 422 on opposite sides of the radial passage 450. The cavities 462 are T-shaped and symmetrically arranged about the radial passage 450.

Figure 17A:
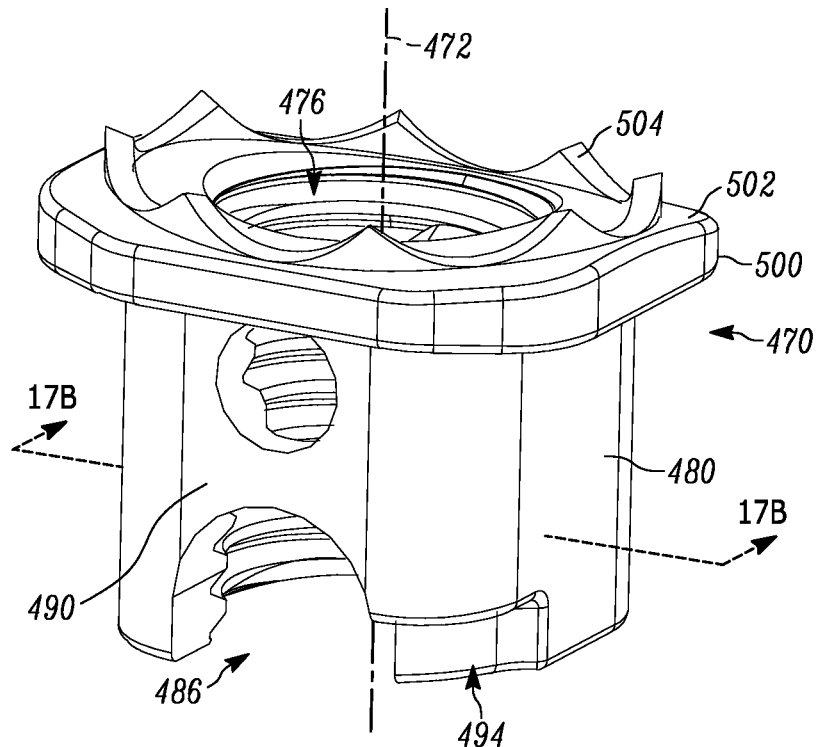
FIG. 17A is a front view of a lift of the spinal cage assembly of FIG. 14.
Figure 17B:
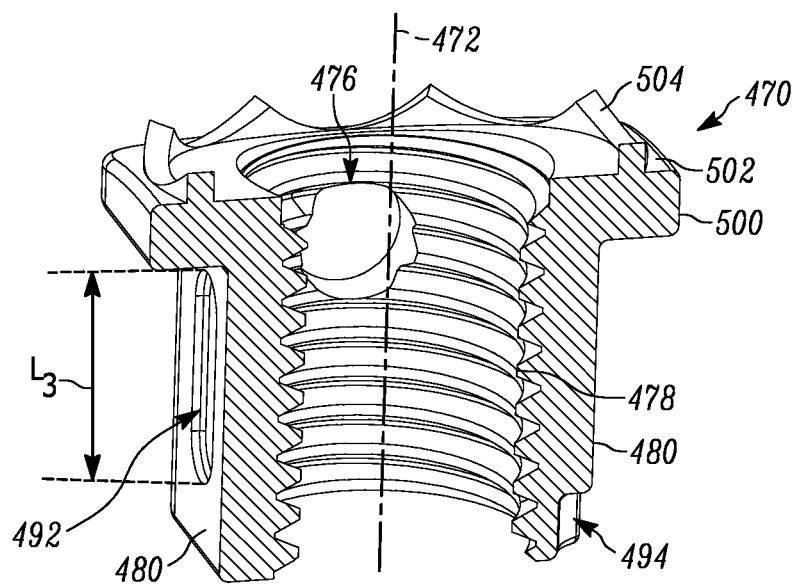
FIG. 17B is a section view of the lift of FIG. 17A taken along line 17B-17B.

Referring to FIGS. 17A-17B, the lift 470 is generally tubular and extends along an axis 472. A threaded inner surface 478 defines an axial bore 476 extending the entire length of the lift 470. Planar surfaces 480, 490 are formed around the exterior of the lift 470 in an alternating manner, i.e., each pair of planar surfaces 480, 490 is diametrically opposed from one another.

A passage 486 extends radially through one of the planar surfaces 490 to the bore 476. A recess 492 extends into one of the planar surfaces 480 and terminates prior to the bore 476. The recess 492 has a length $L_3$ and is oval-shaped. A circumferential notch 494 extends from the radial passage 486 away from the recess 492 to the adjacent planar surface 480.

A flange 500 extends radially outward from the lift 470 and encircles the bore 476. The flange 500 includes an axial end surface 502. Bone engaging structure 504 extends from the end surface 502.

Figure 18A:
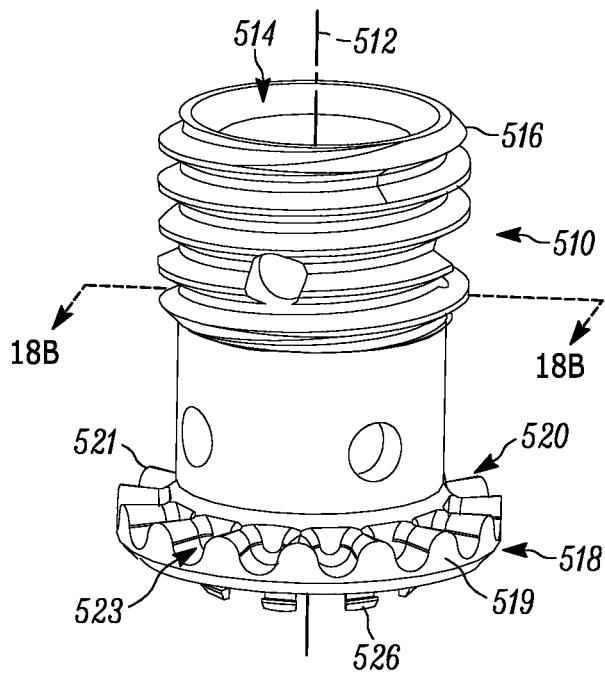
FIG. 18A is a front view of a collar of the spinal cage assembly of FIG. 14.
Figure 18B:
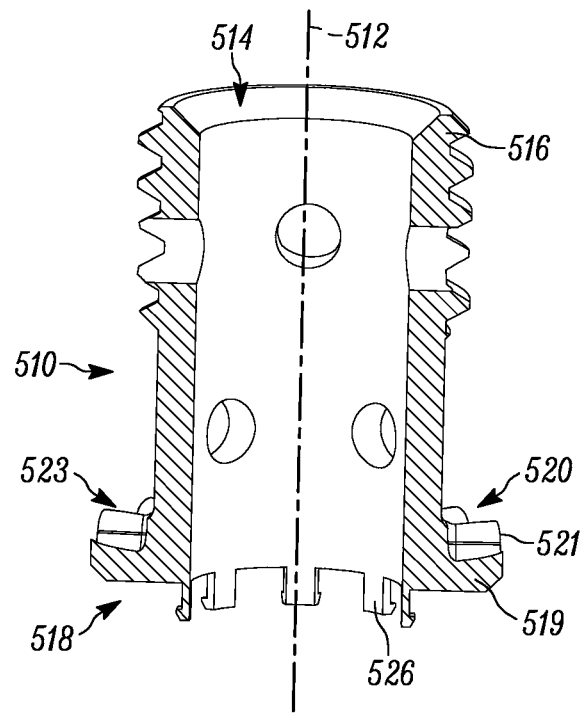
FIG. 18B is a section view of the collar of FIG. 18A taken along line 18B-18B.

As shown in FIGS. 18A-18B, the collar 510 is tubular and extends along an axis 512. An axial bore 514 extends the length of the collar 510. Threads 516 are provided along the exterior of the collar 510. An end 518 of the collar 510 includes a flange 519 extending radially outward. A gearwheel 520 is provided on the flange 519 and encircles the axis 512. The gearwheel 520 includes projections 521 and recesses 523 arranged in an alternating manner around the end 518 of the collar 510 in an endless loop. Resilient tabs 526 extend from the end 518 of the collar 510. As shown, the tabs 526 are L-shaped and extend radially outward.

When the cage assembly 420 is assembled (see FIGS. 14-15), the lift 470 and collar 510 extend within the bore 428 of the housing 422. The gearwheel 520 of the collar 510 rests on the inner surface 438 of the housing 422. The resilient tabs 526 snap over the projection 436 and into the channel 440. Due to this construction, the collar 510 is rotatable about the axis 512 relative to the housing 422 but relative axial movement between the collar and housing is prevented. The tabs 526 therefore slide along the projection 436 within the channel 440 during rotation of the collar 510.

The threads 516 on the collar 516 extend into and threadably engage the threads 478 on the lift 470. The planar surfaces 480, 490 on the lift 470 are radially aligned with and slide along the planar portions 430 of the inner surface 426 of the housing 422. Consequently, the lift 470 is axially moveable relative to the housing 422 but relative rotational movement between the lift and housing is prevented. The distance between the end surface 502 of the flange 500 and the end surface 436 of the housing 422 defines the height $H_3$ of the cage assembly 420 (see FIG. 14).

The pin 524 (see FIG. 15) has the diameter $\Phi_2$ and an enlarged portion 525 having a diameter $\Phi_4$ larger than the diameter $\Phi_1$ of the radial passage 454 but smaller than the diameter $\Phi_3$ of the countersink 457. The pin 524 is passed through the bore 428 into the radial passage 454 such that the enlarged portion 525 is located in the countersink 457 and the remainder of the pin extends within the radial passage. This configuration prevents the pin 524 from moving radially outward and out of the radial passage 454. Moreover, once the collar 510 is threaded to the lift 470 the recess 492 prevents the pin 524 from moving radially inward into the bore 428. In other words, the pin 524 is securely maintained in the radial passage 454. It will be appreciated that either of the pins 124, 324 and associated radial passages 54, 254 could be configured similarly to the pin 524 and radial passage 454.

Figure 15:
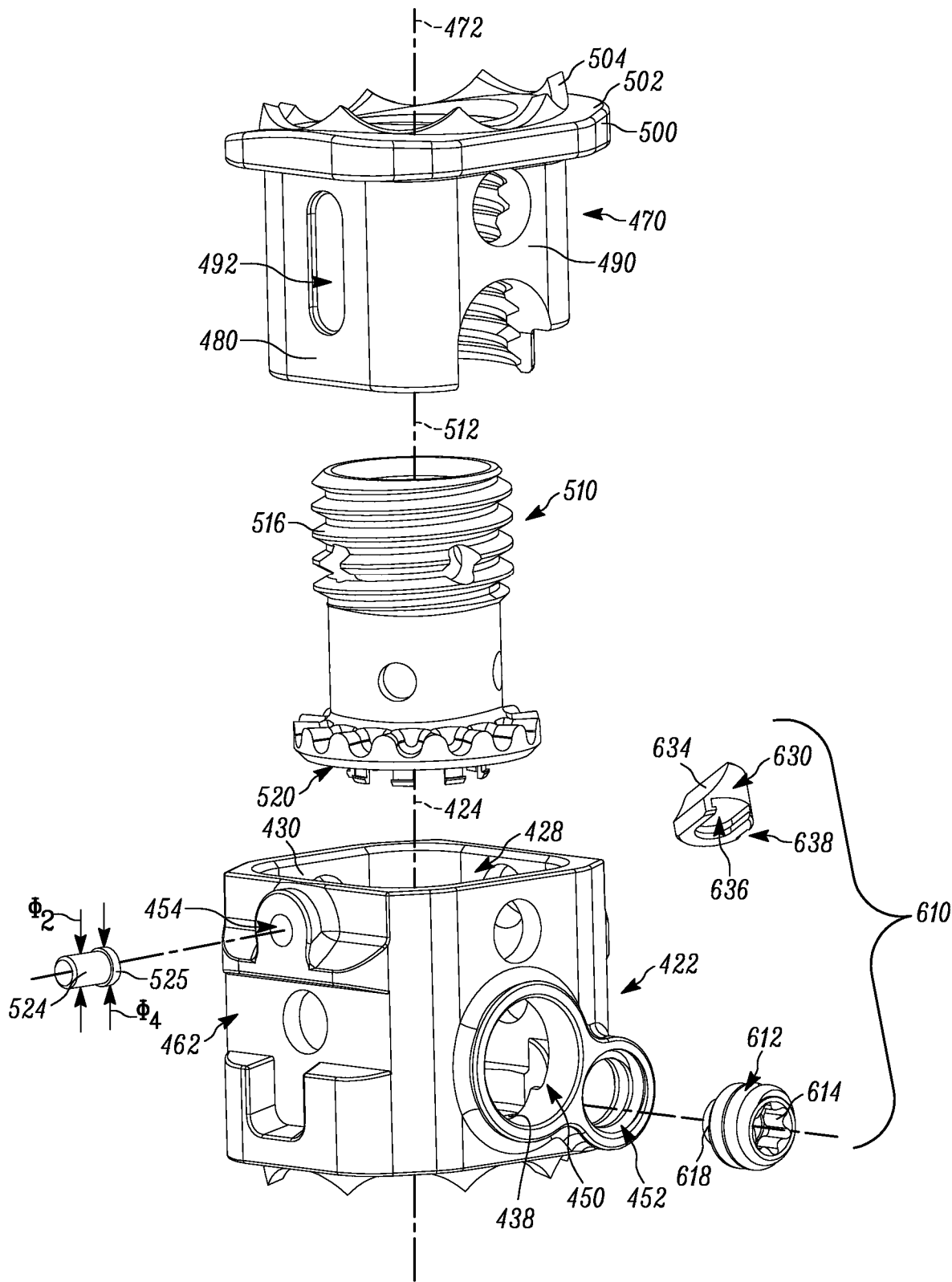
FIG. 15 is an exploded view of the spinal cage assembly of FIG. 14.
Figure 16A:
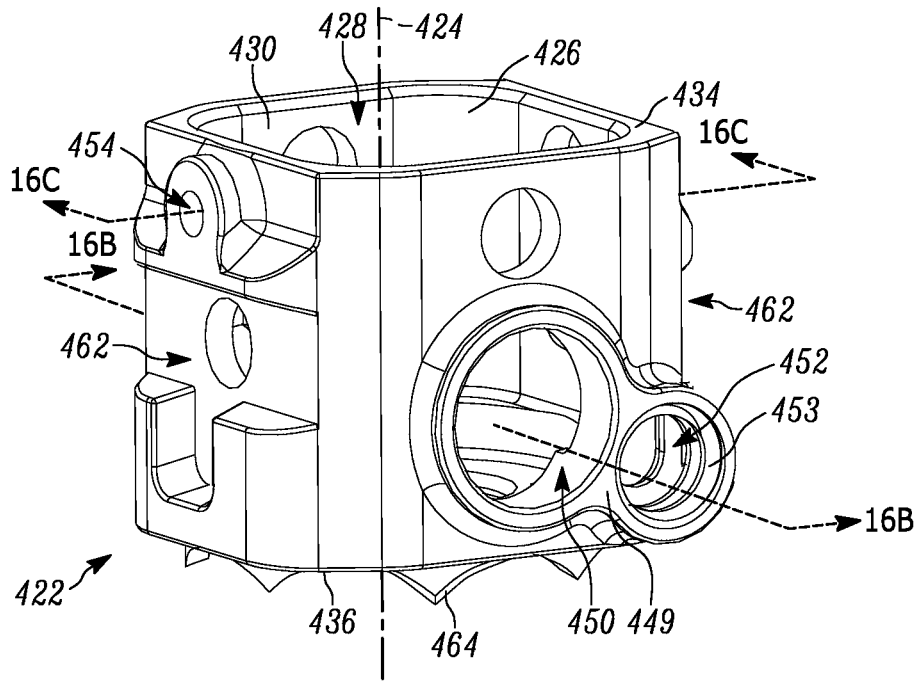
FIG. 16A is a front view of a housing of the spinal cage assembly of FIG. 14.
Figure 16B:
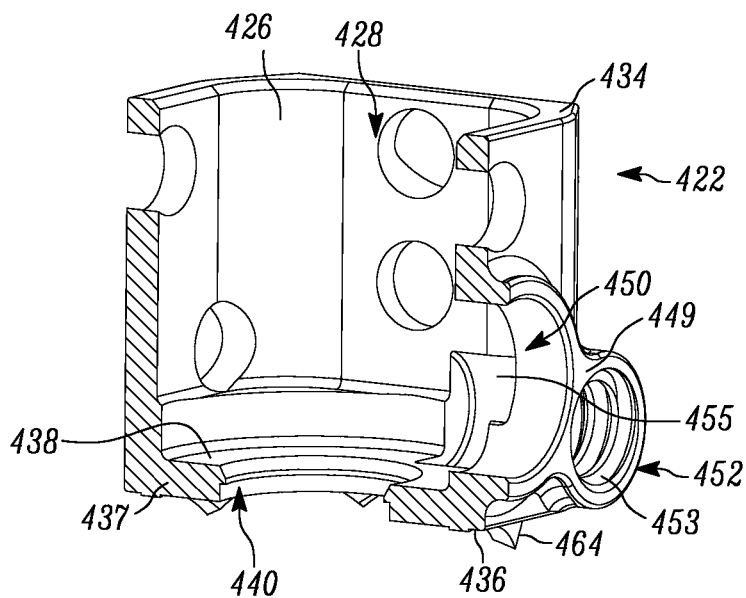
FIG. 16B is a section view of the housing of FIG. 16A taken along line 16B-16B.
Figure 16C:
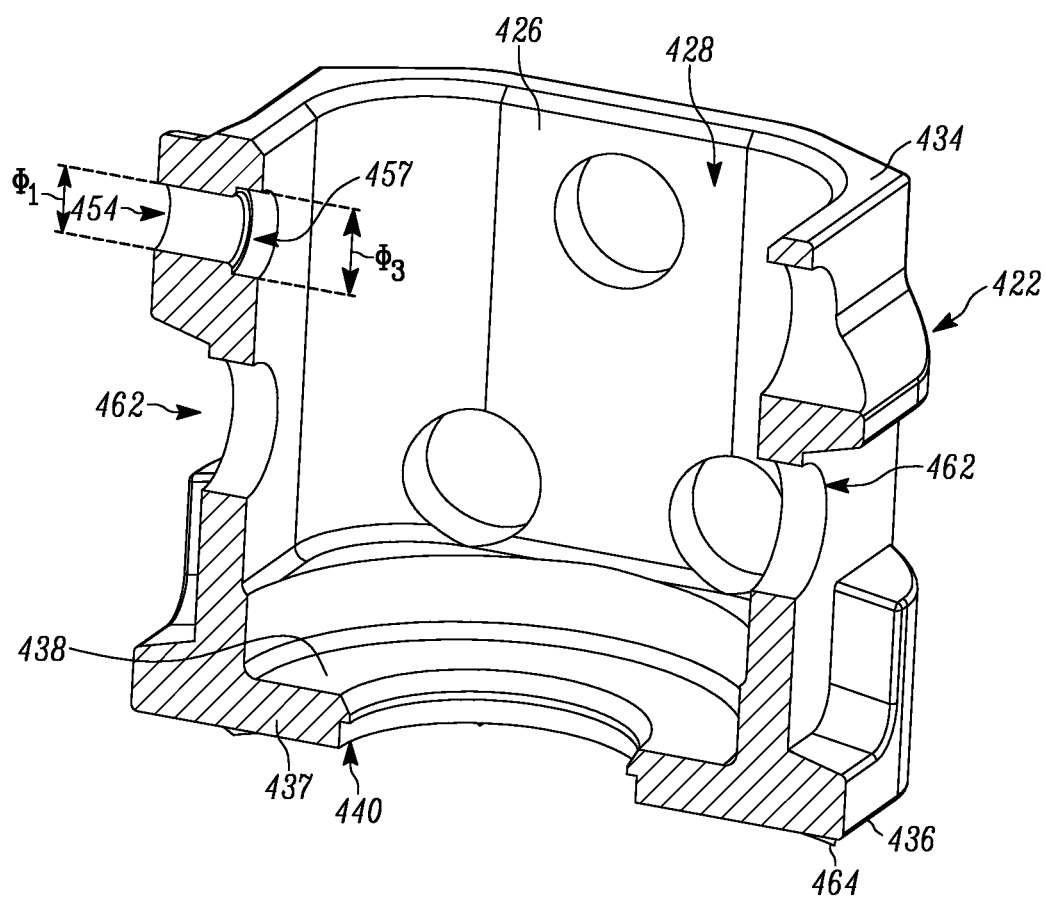
FIG. 16C is a section view of the housing of FIG. 16A taken along line 16C-16C.

Referring to FIG. 15, the locking device 610 is connected to the housing 422 for locking the cage assembly 420 at a specific height $H_3$. The locking device 610 includes a locking screw 612 and a piston 630. The locking screw 612 is threaded along its length and includes a tool receiving portion 614 at one end and a tab 618 at the other end. The tool receiving portion 614 can have a splined, hexagonal, etc. shape. The tab 618 can be T-shaped.

The piston 630 includes a leading arcuate surface 634. In one example, the arcuate surface 634 has similar curvature to the curvature of the gearwheel 520 on the collar 510. A recess or pocket 636 extends into the piston 630 at the end opposite the arcuate surface 634. The pocket 636 is sized and shaped to slidably receive the tab 618 on the locking screw 612 and, thus, the pocket can be T-shaped. A slot 638 extends the length of the piston 630 on a side of the piston opposite the arcuate surface 634.

To assemble the locking device 610, the locking screw 612 is threaded into the threaded portion 453 of the passage 452 with the tool receiving portion 614 exposed/facing away from the housing 422. The tab 618 is positioned in the unthreaded portion 455 of the passage 452 and accessible through the bore 428.

The piston 430 is moved through the bore 428 to the unthreaded portion 455 where the tab 618 on the locking screw 612 is inserted into the pocket 636 such that the arcuate surface 634 faces the bore 428. In one example, the piston 630 is installed upside-down over the tab 618 and rotated 180° to position the arcuate surface 634 facing the bore 528. In this orientation, the slot 638 faces generally away from bore 428. This connection allows the locking screw 612 to rotate relative to the piston 630 but prevents relative axial movement therebetween.

The housing 422 is staked at 640 to deform the housing material into the slot 638 to prevent relative rotation between the piston 630 and the housing.

Figure 19:
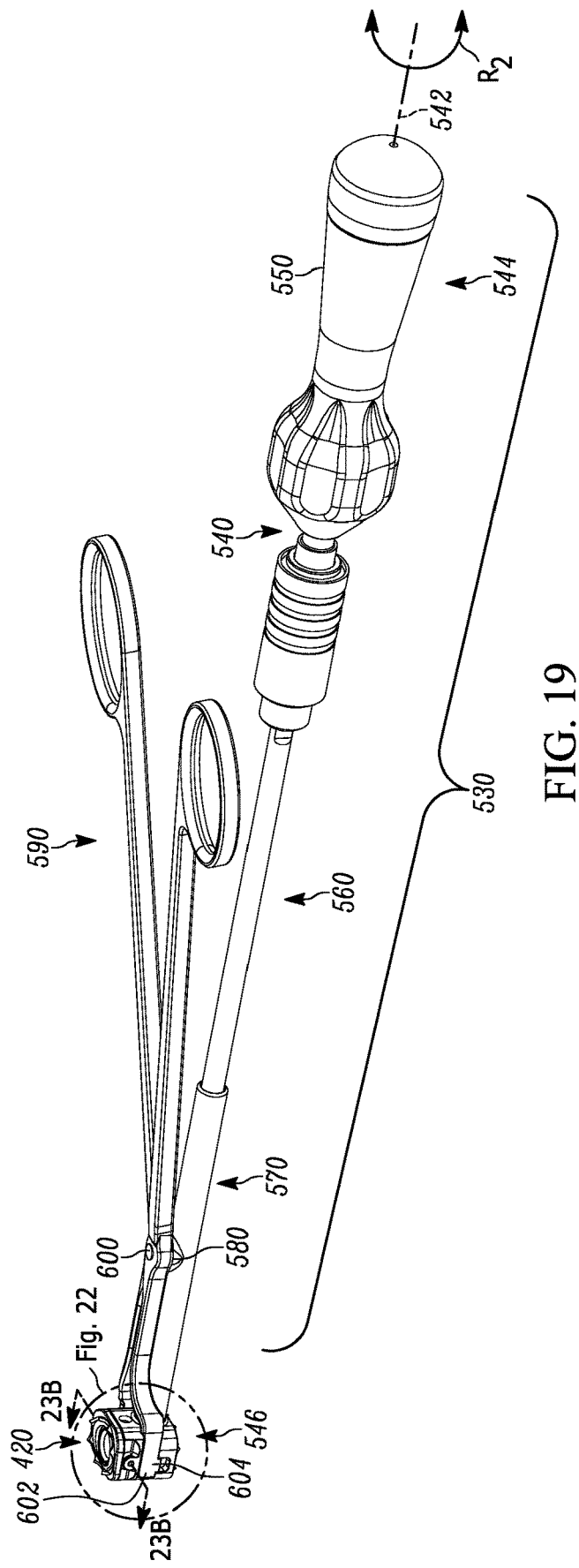
FIGS. 19-21 are views of a tool for installing and adjusting the spinal cage assembly of FIG. 14.
Figure 20:
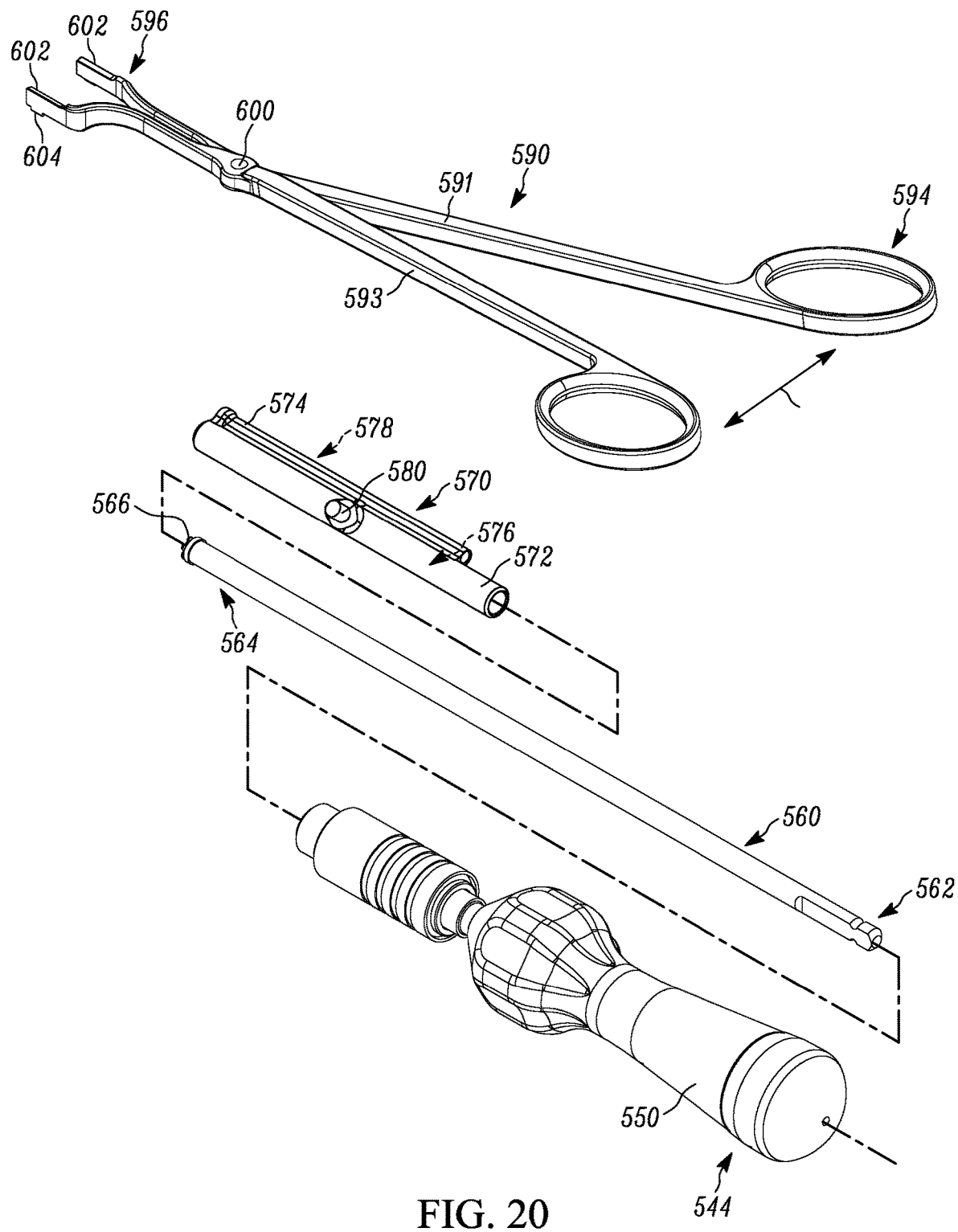
Figure 21:
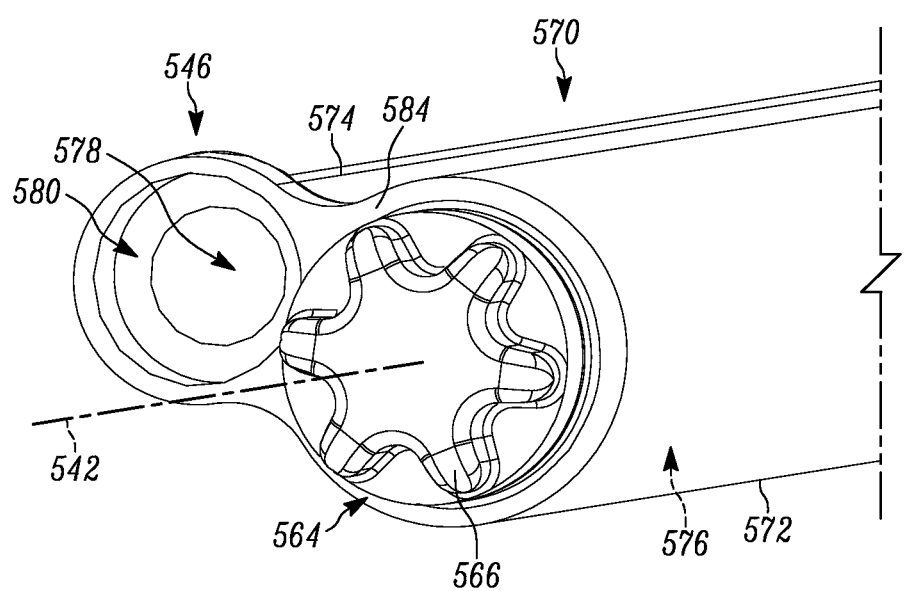
Figure 22:
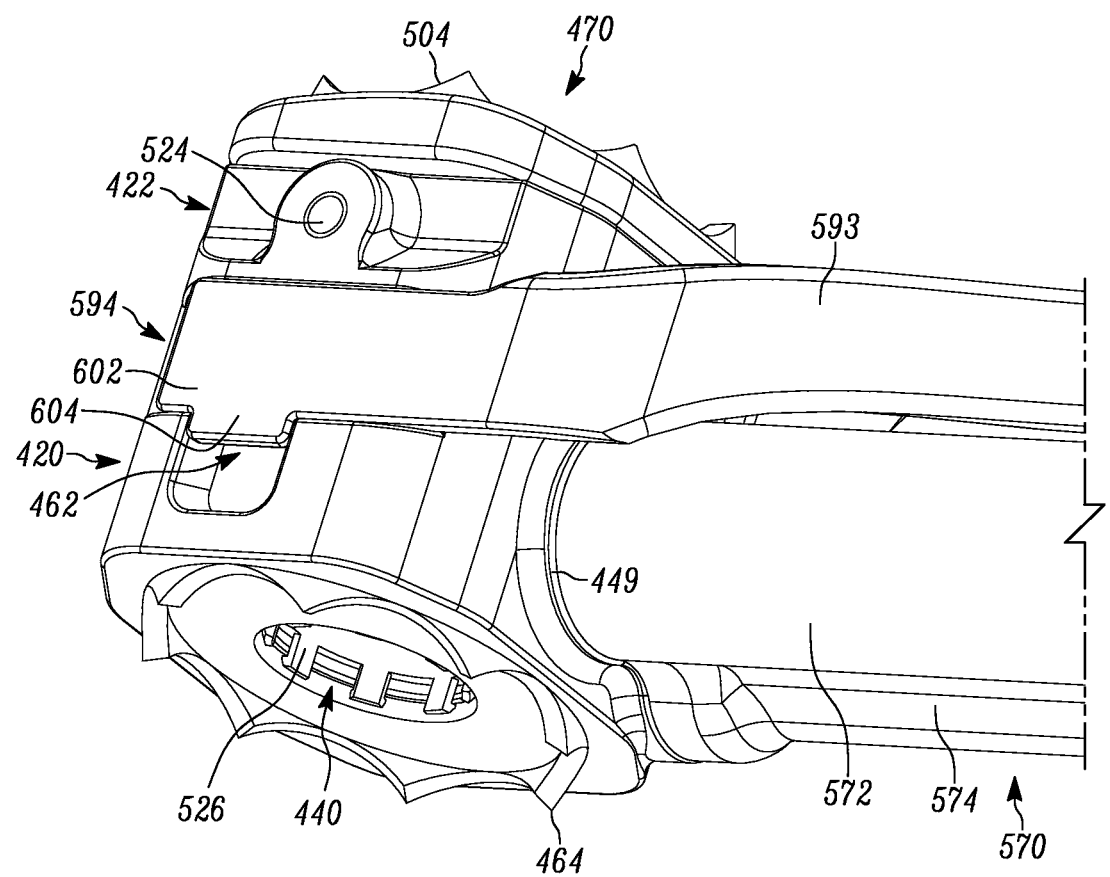
FIG. 22 is an enlarged view of a portion of FIG. 19.

A tool 530 is used to adjust the height $H_3$ of the cage assembly 420. As shown in FIGS. 19-21, the tool 530 includes an expander 540 and a clamp 590. The expander 540 extends along an axis 542 from a first end 544 to a second end 546. A handle 550 is provided at the first end 544 and a sleeve 570 is provided at the second end 546. A shaft 560 connects the handle 550 to the sleeve 570.

The shaft 560 extends from a first end 562 fixed to the handle 550 to a second end 564 having a gearwheel 566. The sleeve 570 includes primary and secondary tubes 572, 574 secured to and extending parallel to one another. Passages 576, 578 extend entirely through the respective primary and secondary tubes 572, 574. A bead 584 (FIG. 21) is provided at the second end 546 of the sleeve 570 and encircles both passages 576, 578. The shaft 560 extends through the passage 576 in the primary tube 572 and is rotatable relative to the primary tube by rotating the handle 550 about the axis 542. A tubular pin 580 extends radially outward from the outside of the first tube 572.

The clamp 590 includes a pair of arms 591, 593 pivotable relative to one another about a sleeve 600 connecting the arms. One end 594 of the arms 591, 593 forms a handle. Another end of each arm 591, 593 includes a projection 602. A tab 604 extends from each projection 602. The projection 602 and tab 604 collectively have the same shape as the recesses 462 in the housing 222.

When the tool 530 is assembled, the sleeve 600 on the clamp 590 extends over the pin 580 on the primary tube 572. This generally aligns the clamp 590 with the expander 540 and positions the projections 602 adjacent the second end 546 of the expander (FIG. 19). The user then operates the handle 594 to position the projections 602 and tabs 604 on each arm 591, 593 within the recesses 462 in the housing 222. Since the clamp 590 and sleeve 470 are connected to one another this positioning automatically aligns the primary tube 572 with the radial opening 450 and aligns the secondary tube 574 with the radial opening 452. The beams 449, 584 automatically abut one another. This fixes the sleeve 570 in place relative to the housing 422 and prevents relative rotational or axial movement therebetween so long as the clamp 590 is inserted into the recesses 462.

That said, the alignment also places the gearwheel 566 on the shaft 560 in meshed engagement with the gearwheel 520 on the collar 510. Consequently, rotating the handle 550 about the axis 542 in the manner $R_2$ causes the lift 470 to move axially relative to the collar and the housing 422. To this end, rotating the collar 510 in the clockwise manner $R_2$ causes the lift 470 to move in the direction $D_4$, thereby increasing the height H3 of the cage assembly 420. On the other hand, rotating the collar 510 in the counterclockwise manner $R_2$ causes the lift 470 to move in the direction $D_5$, thereby decreasing the height $H_3$ of the cage assembly 420. The engagement between the tabs 526 and the channel 440 prevents axial movement of the collar 510 during its rotation in the manner $R_3$.

As the height $H_3$ increases, the bone engaging structures 464, 504 move into engagement with the adjacent vertebrae and apply outward compressive forces against the vertebrae to help hold the cage assembly 20 in place. It will be appreciated that the length $L_3$ of the recess 492 in the lift 470 dictates the range of heights $H_3$ over which the cage assembly 420 can be adjusted. To this end, the pin 524 bottoms out at the end of the recess 492 to prevent additional axial movement of the lift 470 beyond a predetermined amount when the cage assembly 420 reaches the longest possible height $H_3$.

Figure 23A:
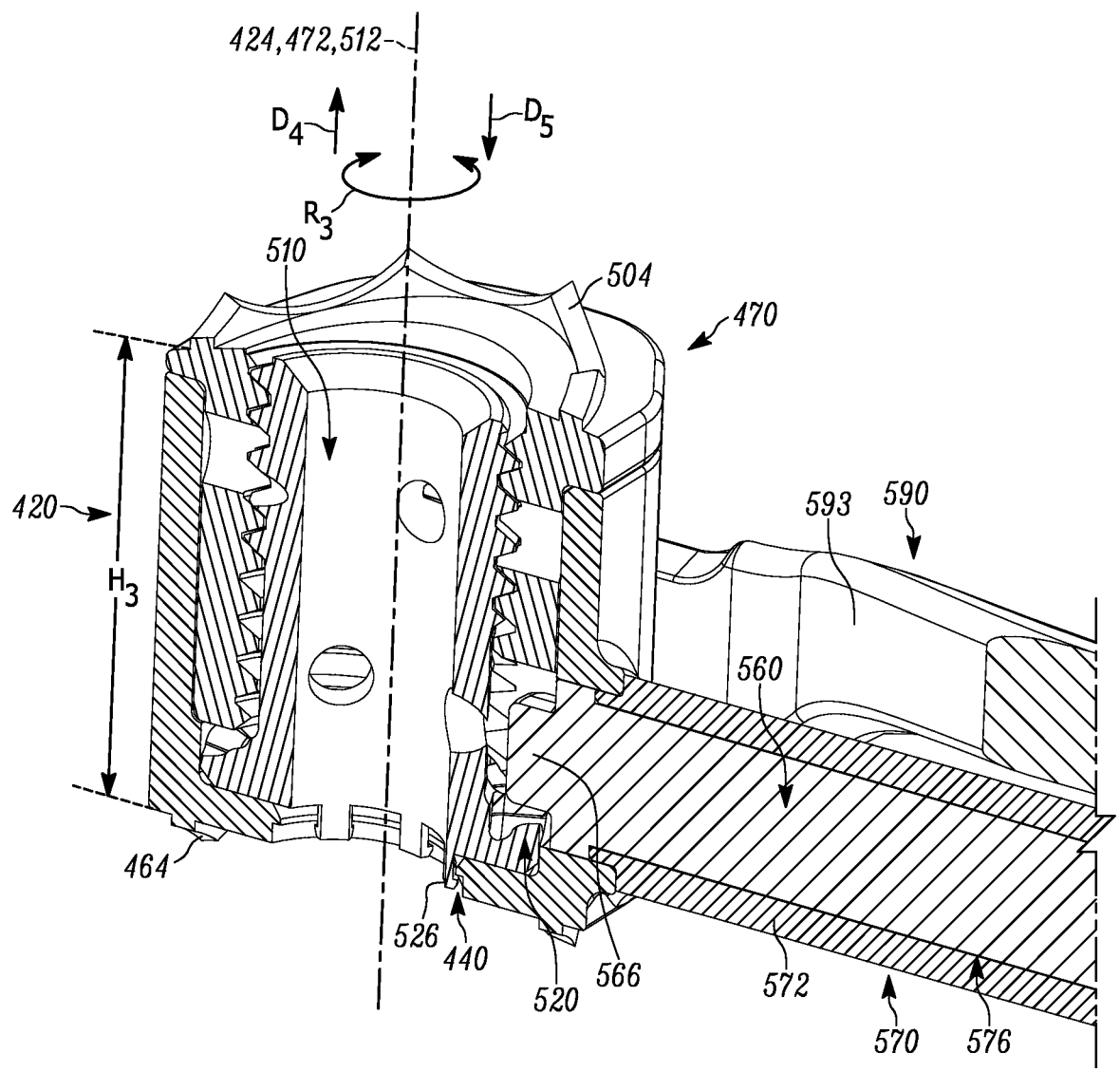
FIG. 23A is first cross-section of the spinal cage assembly of FIG. 14 during installation.
Figure 23B:
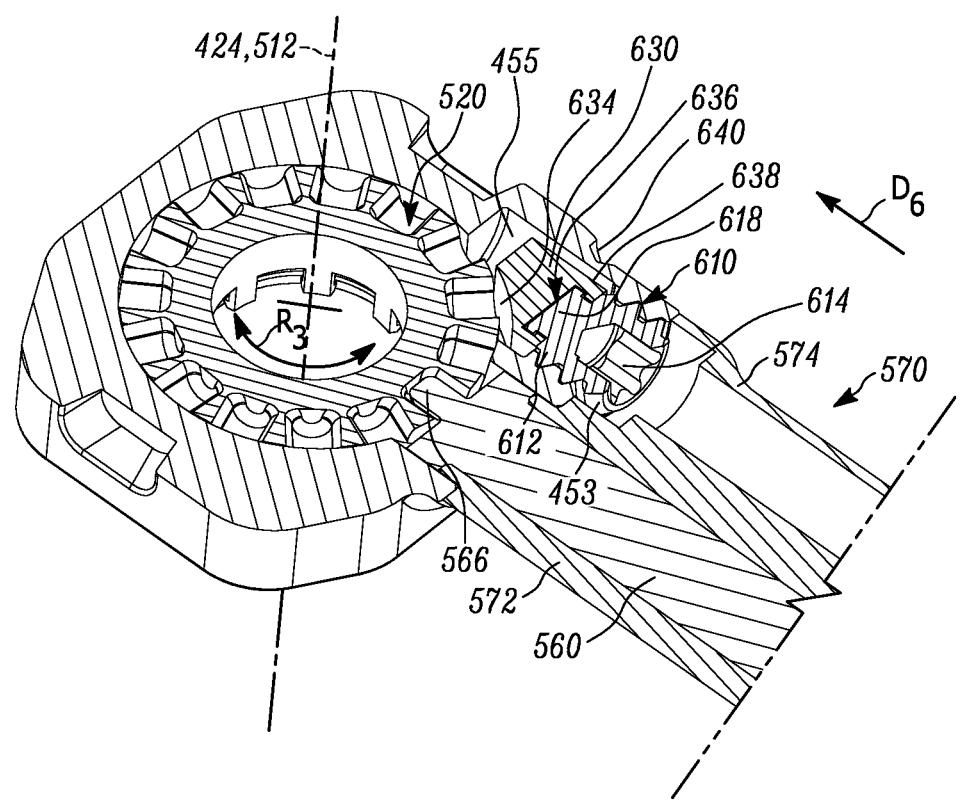
FIG. 23B is a second cross-section of the spinal cage assembly of FIG. 14 during installation.
Figure 23C:
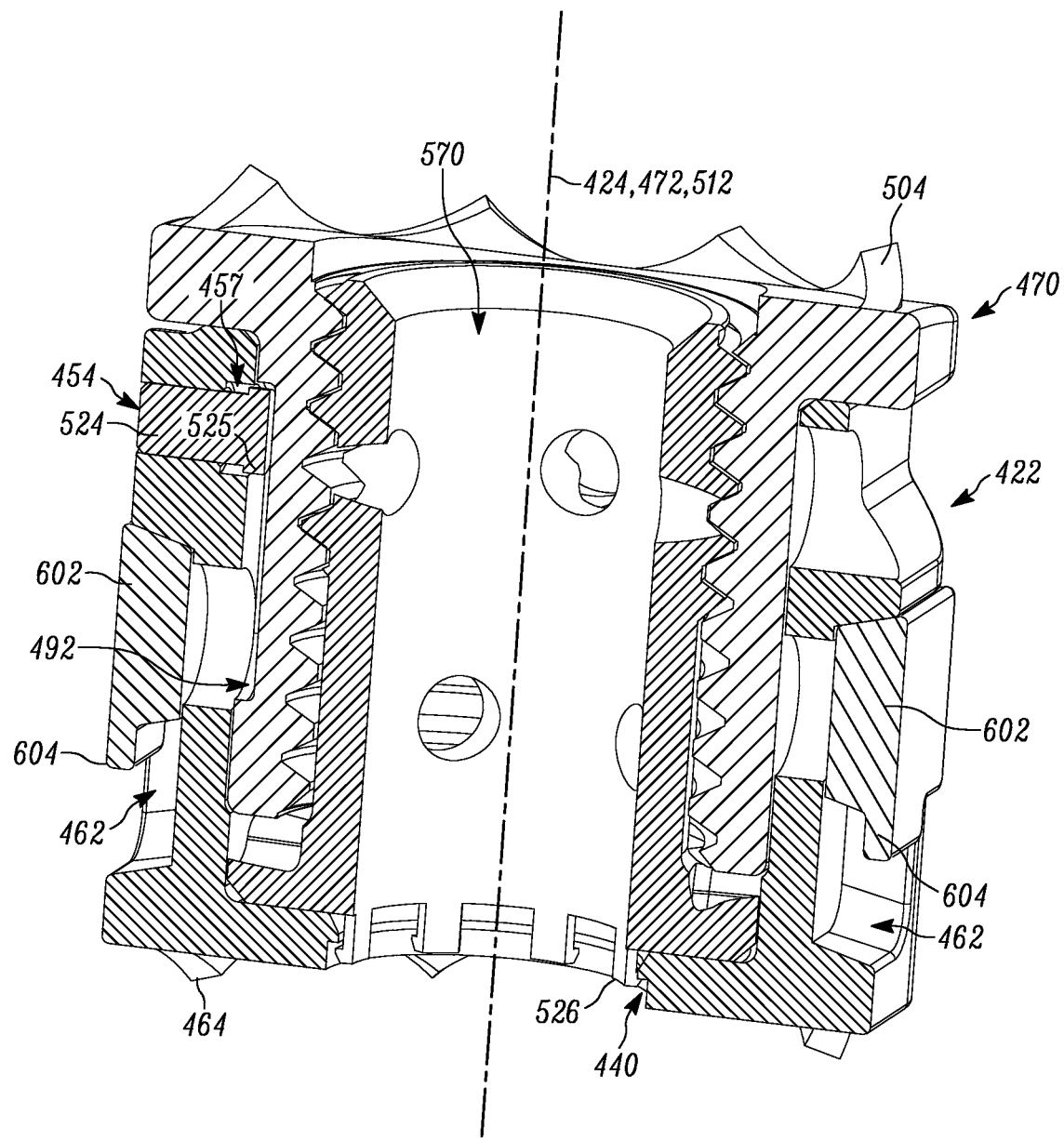
FIG. 23C is a section view of the spinal cage assembly of FIG. 19 taken along line 23C-23C.

Once the cage assembly 420 has the desired height $H_3$, another tool (not shown) is inserted into the secondary tube 574 and engages the tool engaging portion 614 of the locking screw 612 (FIG. 23B). The tool is rotated in the clockwise direction to drive the locking screw 612 further into the radial passage 452 in the direction $D_6$. The piston 630 is therefore driven further into the unthreaded portion 455 of the radial passage 452 until the arcuate surface 634 moves into engagement with the gearwheel 520.

Additional rotation of the tool causes the piston 630 to apply a compressive force to the gearwheel 520 to prevent rotation thereof. The locking device 610 is specifically designed to remain in place and prevent separation from the housing 422. To this end, the staked housing 640 limits the piston 630 to axial/linear movement. Furthermore, the connection between the tab 618 and the pocket 636 prevents the piston 630 and locking screw 612 from separating from one another while in the passage 452 and the collar 510 abutting the inner surface 438. Moreover, the piston 630 is specifically configured to be too large to pass through the threaded portion 453 of the passage 452 and, thus, neither the piston nor the locking screw 612 can be drawn out of the passage 452.

As a result, once the locking device 610 is in place the lift 470 is prevented from moving axially and the cage assembly 420 is fixed at the desired height $H_3$ until/unless the locking screw 612 is backed out of the radial passage 452 sufficient to remove the compressive force of the piston 630 on the gearwheel 520. The handle 594 is then operated to release the clamp 590 from the housing 222, which allows the clamp and expander 540 to be pulled away from the locked cage assembly 420.

The cage assemblies described herein are advantageous for several reasons. The planar surface engagement between the lift and housing prevent relative rotation therebetween. That, along with the engagement between the collar and the projection on the housing that prevents relative axial movement between the collar and housing, provides a more robust, stable implant.

Moreover, since the cage assembly can have module adaptors with bone engaging structure, kits can be made that include a wide array of adaptors for different anatomical and/or surgical conditions. To this end, the adaptors supplied by the kits can have different sizes, shapes, and angles. For example, different adaptors with lordotic angles of 0°, 3°, 8°, and 15° can be provided. The kits can also be provided with lifts of varying length to provide the user with a cage assembly capable of accounting for a range of intervertebral spacing. In one example, the range of heights available for the cage assemblies can include: 12-16 mm, 14-20 mm, 17-25 mm, 22-34 mm, 30-49 mm, and 44-76 mm. Alternative height ranges can include: 20-26 mm, 24-34 mm, 30-46 mm, 40-66 mm, and 60-106 mm. The footprints of the cage assembly can be, for example, 12×14 mm, 14×16 mm, and 16×18 mm.

The bone engaging structure can be configured on the adaptors to provide parallel, kyphotic or lordotic angulation to allow the user to have multiple approach options. The angulations can therefore be, for example, between about −30° and 30° to meet the anatomical needs of the spine.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

The invention claimed is:

1. A spinal implant for placement between first and second vertebrae, comprising:
 a housing having,
  a) an inner surface comprising at least one planar portion,
  b) first and second axial end surfaces,
  c) a bore extending along an axis through the housing and between the end surfaces,
  d) a first projection extending axially away from a perimeter of one of the first and second axial end surfaces and extending at least partially about the axis, and
  e) a channel formed in the first projection and opening radially inward;
 a lift slidably received in the bore and including threads along its length, the lift having at least one planar surface forming at least one flat extending axially along the length of the threads; and
 a collar comprising a flange connected to a gearwheel for rotating the collar, the collar threadably engaged with the lift, and the channel formed in the first projection of the housing accommodating therein the flange and the gearwheel such that the first projection prevents axial movement of the collar relative to the housing,
 wherein rotation of the collar about the axis causes the lift to move axially relative to the collar and the housing for adjusting the height of the implant, and
 wherein the at least one planar portion of the housing cooperates with the at least one flat on the lift to prevent rotation of the lift relative to the housing.

2. The spinal implant of claim 1, wherein the collar includes resilient tabs that form a snap-in connection with the channel to prevent axial movement of the collar relative to the housing.

3. The spinal implant of claim 1, wherein the flange extends radially into the channel formed in the first projection to prevent the axial movement of the collar relative to the housing.

4. The spinal implant of claim 1, wherein the inner surface of the housing defines the bore.

5. The spinal implant of claim 1, wherein the gearwheel is exposed through a first radial passage in the housing for receiving a tool for rotating the collar about the axis.

6. The spinal implant of claim 1, wherein the lift and the housing each includes protrusions integrally formed therewith.

7. The spinal implant of claim 1 further comprising a first adaptor having bone engaging structure formed thereon and a first retaining ring provided on the first adaptor, the first retaining ring having an expanded condition allowing the first adaptor to be moved over a tapered projection on the lift and a collapsed condition locking the first adaptor to the lift.

8. The spinal implant of claim 7, wherein the first adaptor includes an interior recess for receiving the first retaining ring and a radial passage extending to the interior recess and through which ends of the first retaining ring extend.

9. The spinal implant of claim 8, wherein in the collapsed condition the first retaining ring extends into a recess in the tapered projection on the lift.

10. The spinal implant of claim 7, wherein moving the first adaptor onto the tapered projection automatically moves the first retaining ring to the expanded condition.

11. The spinal implant of claim 7, wherein the first adaptor includes a plurality of projections that interdigitate with recesses on the lift when the first retaining ring is in the collapsed condition.

12. The spinal implant of claim 7 further comprising a second adaptor having bone engaging structure formed thereon and a second retaining ring provided on the second adaptor, the second retaining ring having an expanded condition allowing the second adaptor to be moved over a tapered second projection on the housing and a collapsed condition locking the second adaptor to the housing.

13. The spinal implant of claim 12, wherein the second adaptor includes a plurality of projections that interdigitate with recesses on the housing when the second retaining ring is in the collapsed condition.

14. The spinal implant of claim 1, wherein the housing includes a second radial passage aligned with an axially extending recess in the lift, a pin extending through the second radial passage into the recess to limit axial movement of the lift relative to the housing, the pin having an enlarged portion positioned within a countersink of the second radial passage to prevent radial movement of the pin outward through the second radial passage.

15. The spinal implant of claim 1 further comprising a locking device including a locking screw and a piston provided in a passage extending through the housing to the bore, rotation of the locking screw causing axial movement of the piston into engagement with the collar to prevent rotation thereof.

16. The spinal implant of claim 15, wherein the housing is staked into a longitudinally extending slot in the piston to prevent rotation of the piston.

17. The spinal implant of claim 15, wherein the piston is sized to be prevented from passing through the passage in the housing.

18. The spinal implant of claim 1, further comprising:
 a tapered projection extending from an end of the housing and including a recess extending about the axis;
 a first adaptor having bone engaging structure formed thereon and a first retaining ring provided on the first adaptor, the first retaining ring having an expanded condition allowing the first adaptor to be moved over the tapered projection on the housing and a collapsed condition locking the first adaptor to the housing;
 a tapered projection extending from an end of the lift and including a recess extending about the axis;
 a second adaptor having bone engaging structure formed thereon and a second retaining ring provided on the second adaptor, the second retaining ring having an expanded condition allowing the second adaptor to be moved over the tapered projection on the lift and a collapsed condition locking the second adaptor to the lift,
 wherein rotation of the collar about the axis causes the lift and the second adaptor to move axially relative to the housing for adjusting the height of the implant.

19. The spinal implant of claim 18, wherein an inner surface of the housing defines the bore and includes at least one planar portion that cooperates with at least one planar surface on the lift to prevent rotation of the lift relative to the housing.

20. The spinal implant of claim 18, wherein in the collapsed condition the first retaining ring extends into a recess in the tapered projection on the housing.

21. The spinal implant of claim 18, wherein in the collapsed condition the second retaining ring extends into a recess in the tapered projection on the lift.

22. The spinal implant of claim 18, wherein the housing includes a second projection extending at least partially about the axis and including a channel, the collar extending into the channel such that the second projection prevents axial movement of the collar relative to the housing.

23. The spinal implant of claim 22, wherein the collar includes resilient tabs that form a snap-in connection with the channel to prevent axial movement of the collar relative to the housing.

24. The spinal implant of claim 22, wherein the collar includes a flange extending radially into the channel to prevent axial movement of the collar relative to the housing.

25. The spinal implant of claim 18, wherein the housing includes a radial passage aligned with an axially extending recess in the lift, a pin extending through the radial passage into the recess to limit axial movement of the lift relative to the housing, the pin having an enlarged portion positioned within a countersink of the radial passage to prevent radial movement of the pin outward through the radial passage.

26. The spinal implant of claim 18 further comprising a locking device including a locking screw and a piston provided in a passage extending through the housing to the bore, rotation of the locking screw causing axial movement of the piston into engagement with the collar to prevent rotation thereof.

27. The spinal implant of claim 26, wherein the housing is staked into a longitudinally extending slot in the piston to prevent rotation of the piston.

28. The spinal implant of claim 26, wherein the piston is sized to be prevented from passing through the passage in the housing.

* * * * *